(12) United States Patent
Hiyoshi et al.

(10) Patent No.: US 7,632,954 B2
(45) Date of Patent: Dec. 15, 2009

(54) SUBSTITUTED SYM-TRIINDOLE

(75) Inventors: Hidetaka Hiyoshi, Shizuoka (JP);
Hironobu Kumagai, Saitama (JP);
Hideo Ooi, Shizuoka (JP)

(73) Assignee: Ihara Chemical Industry Co., Ltd. (JP)

( * ) Notice: Subject to any disclaimer, the term of this patent is extended or adjusted under 35 U.S.C. 154(b) by 343 days.

(21) Appl. No.: 10/589,534

(22) PCT Filed: Feb. 14, 2005

(86) PCT No.: PCT/JP2005/002140

§ 371 (c)(1),
(2), (4) Date: Aug. 15, 2006

(87) PCT Pub. No.: WO2005/077956

PCT Pub. Date: Aug. 25, 2005

(65) Prior Publication Data

US 2007/0191455 A1   Aug. 16, 2007

(30) Foreign Application Priority Data

Feb. 16, 2004   (JP)   ............... 2004-038874

(51) Int. Cl.
*C07D 487/22* (2006.01)
(52) U.S. Cl. .................................... 548/416
(58) Field of Classification Search .............. 548/400, 548/416
See application file for complete search history.

(56) References Cited

U.S. PATENT DOCUMENTS 7,205,071 B2 *   4/2007   Kaneko et al. ........... 429/218.1

FOREIGN PATENT DOCUMENTS

| JP | 2001-261680 | 9/2001 |
| JP | 2001-288239 | 10/2001 |
| JP | 2003-249221 | 9/2003 |
| JP | 2003-272865 | 9/2003 |
| JP | 2004-123619 | 4/2004 |

OTHER PUBLICATIONS

Robertson, Neil. Preparation, X-ray structure and properties of a hexabrominated symmetric indole trimer and its TCNQ adduct: a new route to functional molecular systems. Journal of Materials Chemistry, 10 (2000) 2043-2047.*

Black, David StC., Synthesis of Biindolyls by the Reaction of Indoles with Indolin-2-ones and Phosphoryl Chloride or Trifluoromethanesulfonic Anhydride. Tetrahedron. 52(13) (1996) 4697-4708.*

Lor-Gomez, Berta. Synthesis of a Triaza Analogue of Crushed-Fullerene by Intramolecular Palladium-Catalyzed Arylation. Organic Letters 6(17) (2004) 2993-2996.*

Manini et al, Acid-Promoted Competing Pathways in the Oxidative Polymerization of 5,6-Dihydroxyindoles and Related Compounds: Straightforward Cyclotrimerization Routes to Diindolocarbazole Derivatives, J. Org. Chem., 1998, 63, 7002-7008.

* cited by examiner

*Primary Examiner*—Kamal A Saeed
*Assistant Examiner*—Samantha L Shterengarts
(74) *Attorney, Agent, or Firm*—Bacon & Thomas, PLLC

(57) ABSTRACT

A novel substituted Sym-triindole derivative that is applicable to a wide spectrum of uses, such as various electrification preventions, electrification controls, capacitors, batteries, chemical sensors, displays, organic EL materials, solar cells, photodiodes, phototransistors, nonlinear materials, photorefractive materials, rustproof agents, adhesives, fibers, antistatic paints, electrodeposition paints, plating primers, electric corrosion protections and the like. There is provided a substituted Sym-triindole derivative of the general formula (1)

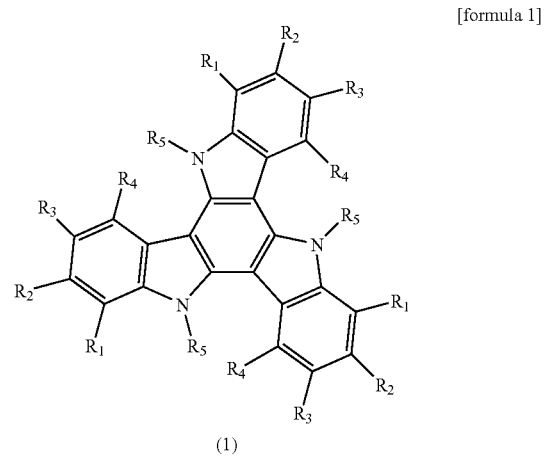

(wherein $R_1$, $R_2$, $R_3$ and $R_4$ are each independently hydrogen, a halogen, a C1-C6 alkyl or the like, provided that, in no event, all of $R_1$, $R_2$, $R_3$ and $R_4$ are hydrogen simultaneously).

11 Claims, 2 Drawing Sheets

SUBSTITUTED SYM-TRIINDOLE

TECHNICAL FIELD

The present invention provides a novel substituted Sym-triindole derivative and a process for production thereof. The substituted Sym-triindole derivative of the present invention is applicable to a wide spectrum of uses, such as various electrification preventions, electrification controls, capacitors, batteries, chemical sensors, displays, organic EL materials, solar cells, photodiodes, phototransistors, nonlinear materials, photorefractive materials, rustproof agents, adhesives, fibers, antistatic paints, electrodeposition paints, plating primers, electric corrosion protections and the like.

BACKGROUND ART

Di-substituted Sym-triindole derivatives are reported. However, with the synthesis process therefor, it has been difficult to synthesize a tri- or higher-substituted Sym-triindole derivative. (See Patent Literature 1.)

Patent Literature 1: JP-A-2000-105139

DISCLOSURE OF THE INVENTION

Task to be Achieved by the Invention

The present invention aims at providing a novel substituted Sym-triindole derivative which is applicable to a wide spectrum of uses, such as various electrification preventions, electrification controls, capacitors, batteries, chemical sensors, displays, organic EL materials, solar cells, photodiodes, phototransistors, nonlinear materials, photorefractive materials, rustproof agents, adhesives, fibers, antistatic paints, electrodeposition paints, plating primers, electric corrosion protections and the like.

Means for Achieving the Task

In view of the above-mentioned situation, the present inventor made a study on the process for producing a substituted Sym-triindole derivative. As a result, it was found unexpectedly that, by reacting a substituted oxyindole with a phosphorus oxyhalide such as phosphorus oxychloride or the like, a tri- or higher-substituted Sym-triindole derivative can be synthesized selectively, that is, the above-mentioned task can be achieved. The finding has led to the completion of the present invention.

Effect of the Invention

By the present invention, there can be provided a novel substituted Sym-triindole derivative which is applicable to a wide spectrum of uses, such as various electrification preventions, electrification controls, capacitors, batteries, chemical sensors, displays, organic EL materials, solar cells, photodiodes, phototransistors, nonlinear materials, photorefractive materials, rustproof agents, adhesives, fibers, antistatic paints, electrodeposition paints, plating primers, electric corrosion protections and the like.

BEST MODE FOR CARRYING OUT THE INVENTION

Figure 1:
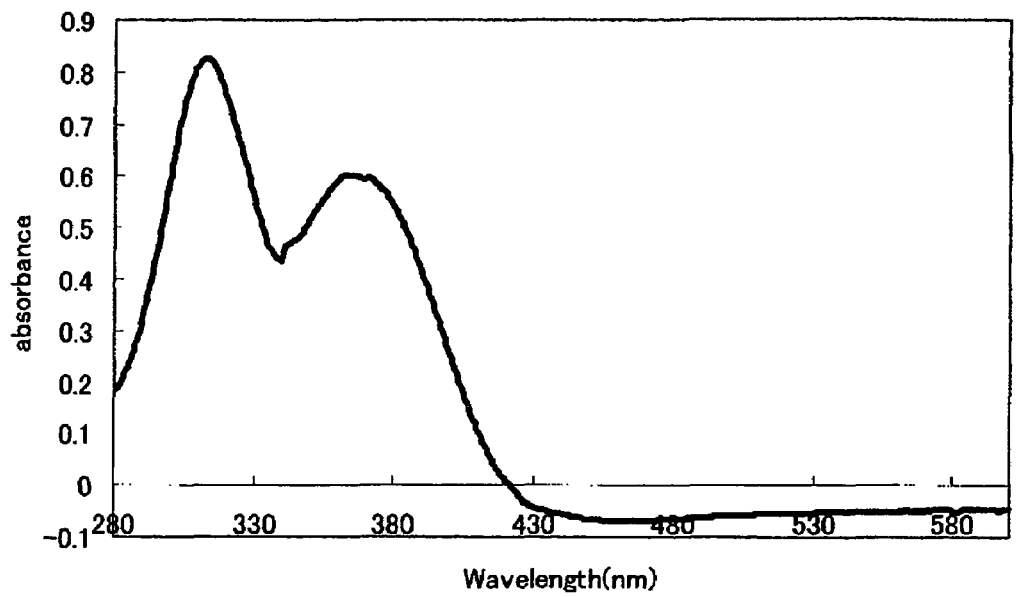
FIG. 1 shows an absorption spectrum in a visible-to-ultraviolet light region of Sym-N-(n-hexyl)-5-(4-formylphenyl)triindole (formula 36).

The present invention is described in detail below. The present invention provides inventions described in the following [1] to [14].

[1] A substituted Sym-triindole derivative represented by the following general formula (1)

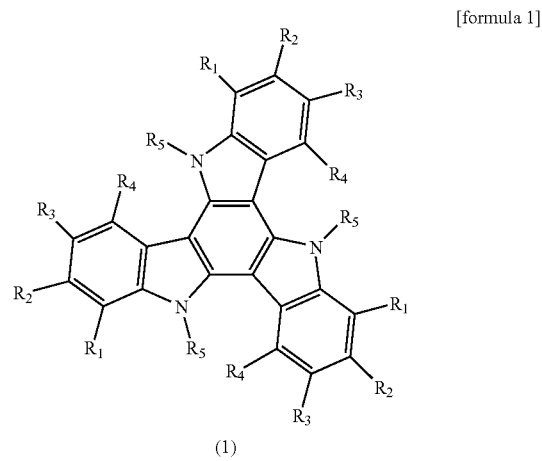

[formula 1]

(1)

(wherein $R_1$, $R_2$, $R_3$ and $R_4$ are each independently hydrogen, halogen, C1-C6 alkyl group, C1-C6 haloalkyl group, substituted C1-C6 alkyl group, C2-C6 alkenyl group, substituted C2-C6 alkenyl group, C2-C6 alkynyl group, substituted C2-C6 alkynyl group, hydroxyl group, C1-C6 alkoxy group, aryloxy group, amino group, mono-substituted amino group, di-substituted amino group, acylamino group, mercapto group, C1-C6 alkylsulfenyl group, C1-C6 haloalkylsulfenyl group, arylsulfenyl group, substituted arylsulfenyl group, C1-C6 alkylsulfinyl group, C1-C6 haloalkylsulfinyl group, aralkylsulfenyl group, arylsulfinyl group, substituted arylsulfinyl group, C1-C6 alkylsulfonyl group, C1-C6 haloalkylsulfonyl group, arylsulfonyl group, substituted arylsulfonyl group, sulfonic acid group (hydroxysulfonyl group), aryl group, substituted aryl group, cyano group, nitro group, formyl group, acyl group, carboxyl group, $C_1$-$C_6$ alkoxycarbonyl group, carbamoyl group, N-mono-substituted carbamoyl group, N,N-di-substituted carbamoyl group, hydrazonomethyl group (—CH=N—NH$_2$ group), N-mono-substituted hydrazonomethyl group, N,N-di-substituted hydrazonomethyl group, oximemethyl group (hydroxyiminomethyl group), C1-C6 alkoxyiminomethyl group, or aryloxyiminomethyl group; $R_5$ is C2-C12 alkyl group, substituted C2-C12 alkyl group, C2-C12 haloalkyl group, or aryl C1-C6 alkyl group; in no event, all of $R_1$, $R_2$, $R_3$ and $R_4$ are hydrogen simultaneously).

[2] A process for producing a substituted Sym-triindole derivative represented by the following general formula (1)

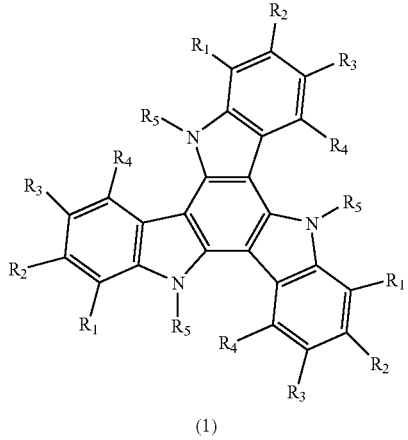

(1)

(wherein $R_1$, $R_2$, $R_3$ and $R_4$ are each independently hydrogen, halogen, C1-C6 alkyl group, C1-C6 haloalkyl group, substituted C1-C6 alkyl group, C2-C6 alkenyl group, substituted C2-C6 alkenyl group, C2-C6 alkynyl group, substituted C2-C6 alkynyl group, hydroxyl group, C1-C6 alkoxy group, aryloxy group, amino group, mono-substituted amino group, di-substituted amino group, acylamino group, mercapto group, C1-C6 alkylsulfenyl group, C1-C6 haloalkylsulfenyl group, aralkylsulfenyl group, arylsulfenyl group, substituted arylsulfenyl group, C1-C6 alkylsulfinyl group, C1-C6 haloalkylsulfinyl group, arylsulfinyl group, substituted arylsulfinyl group, C1-C6 alkylsulfonyl group, C1-C6 haloalkylsulfonyl group, arylsulfonyl group, substituted arylsulfonyl group, sulfonic acid group (hydroxysulfonyl group), aryl group, substituted aryl group, cyano group, nitro group, formyl group, acyl group, carboxyl group, C1-C6 alkoxycarbonyl group, carbamoyl group, N-mono-substituted carbamoyl group, N,N-di-substituted carbamoyl group, hydrazonomethyl group (—CH=N—NH$_2$ group), N-mono-substituted hydrazonomethyl group, N,N-di-substituted hydrazonomethyl group, oximemethyl group (hydroxyiminomethyl group), C1-C6 alkoxyiminomethyl group, or aryloxyiminomethyl group; $R_5$ is C2-C12 alkyl group, substituted C2-C12 alkyl group, C2-C12 haloalkyl group, or aryl C1-C6 alkyl group; in no event, all of $R_1$, $R_2$, $R_3$ and $R_4$ are hydrogen simultaneously), which process comprises reacting a substituted oxyindole represented by the following general formula (2)

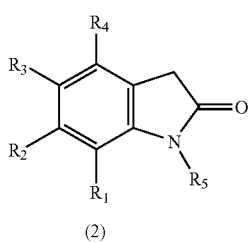

(2)

(wherein $R_1$, $R_2$, $R_3$, $R_4$ and $R_5$ have the same definitions as given above) with a phosphorus oxyhalide.

[3] A Sym-triindole derivative represented by the following general formula (3)

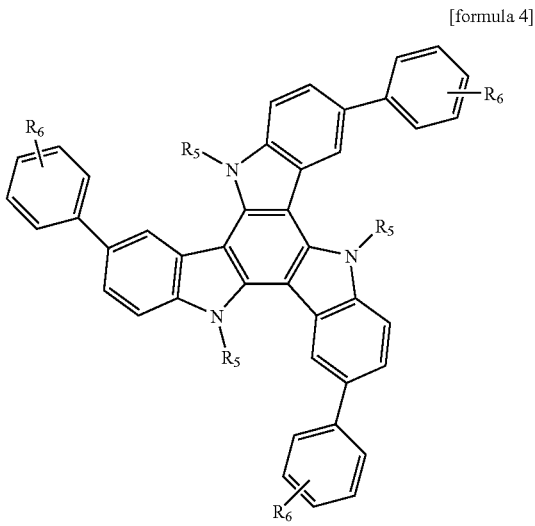

(3)

(wherein $R_5$ is C2-C12 alkyl group, substituted C2-C12 alkyl group, C2-C12 haloalkyl group, or aryl C1-C6 alkyl group; and $R_6$ is hydrogen, formyl group, cyano group, C1-C6 alkoxycarbonyl group, dicyanovinyl group, aryl group or substituted aryl group).

[4] A process for producing a Sym-triindole derivative represented by the following general formula (7)

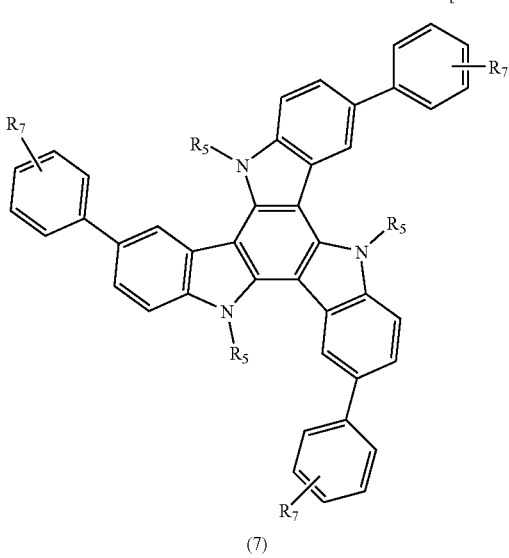

(7)

(wherein $R_5$ is C2-C12 alkyl group, substituted C2-C12 alkyl group, C2-C12 haloalkyl group or aryl C1-C6 alkyl group; and $R_7$ is hydrogen, formyl group, cyano group, C1-C6 alkoxycarbonyl group, aryl group or substituted aryl group), which process comprises reacting an N-substituted-5-halo-oxyindole represented by the following general formula (4)

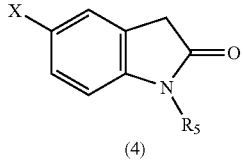

(wherein $R_5$ has the same definition as given above; and X is halogen) with a phosphorus oxyhalide to obtain an N-substituted-5-halo-triindole derivative represented by the following general formula (5)

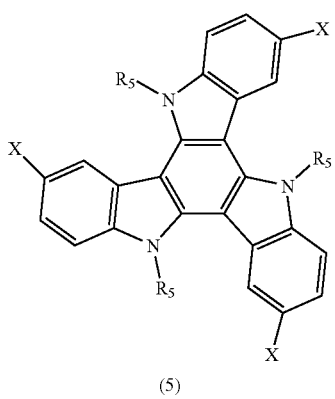

(wherein $R_5$ and X have the same definitions as given above) and further reacting it with a boric acid compound represented by the following general formula (6)

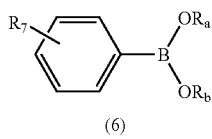

(wherein $R_7$ has the same definition as give above; and $R_a$ and $R_b$ are each independently hydrogen atom, C1-C6 alkyl group or optionally substituted phenyl group and may be combined to each other to form a ring).

[5] A process for producing a Sym-triindole derivative represented by the following general formula (7)

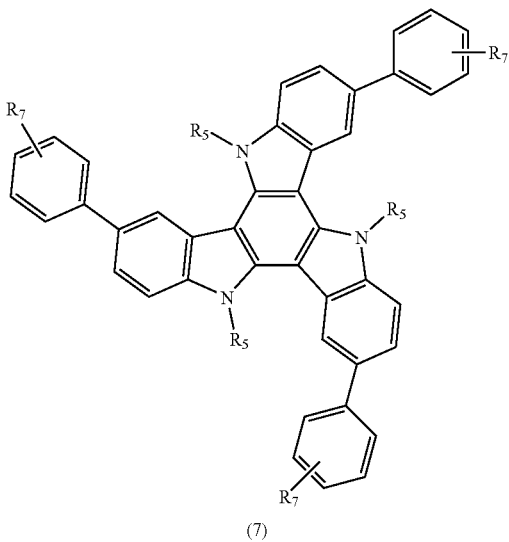

(wherein $R_5$ is C2-C12 alkyl group, substituted C2-C12 alkyl group, C2-C12 haloalkyl group or aryl C1-C6 alkyl group; and $R_7$ is hydrogen, formyl group, cyano group, C1-C6 alkoxycarbonyl group, aryl group or substituted aryl group), which process comprises reacting an N-substituted-5-halo-triindole derivative represented by the following general formula (5)

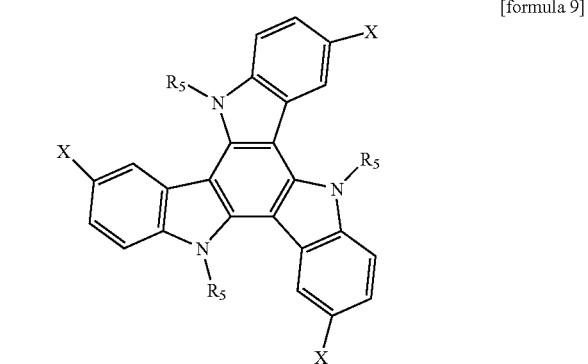

(wherein $R_5$ has the same definition as given above; and X is halogen) with a boric acid compound represented by the following general formula (6)

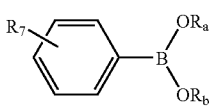

(wherein $R_7$ has the same definition as given above; and $R_a$ and $R_b$ are each independently hydrogen atom, C1-C6 alkyl group or optionally substituted phenyl group and may be combined to each other to form a ring).

[6] A process for producing an N-substituted-5-halo-triindole derivative represented by the following general formula (5)

[formula 13]

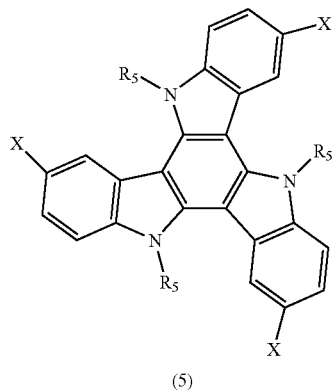

(5)

(wherein $R_5$ is C2-C12 alkyl group, substituted C2-C12 alkyl group, C2-C12 haloalkyl group or aryl C1-C6 alkyl group; and X is halogen), which process comprises reacting an N-substituted-5-halo-oxyindole represented by the following general formula (4)

[formula 12]

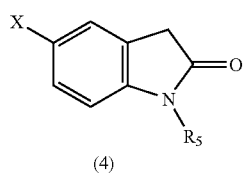

(4)

(wherein $R_5$ and X have the same definitions as given above) with a phosphorus oxyhalide.

[7] A process for producing a Sym-triindole derivative represented by the following general formula (10)

[formula 16]

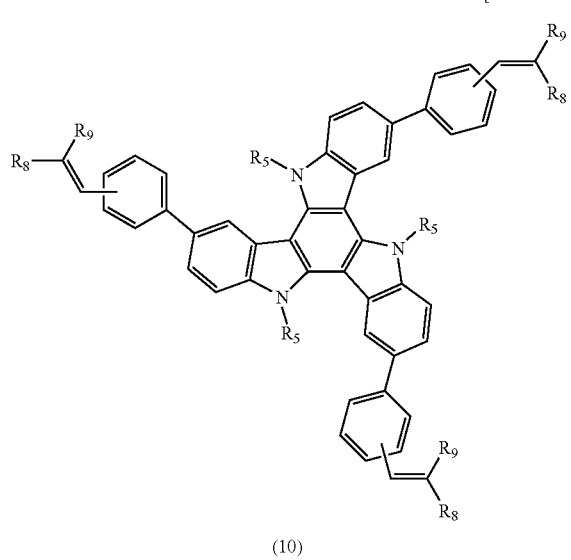

(10)

(wherein $R_5$ is C2-C12 alkyl group, substituted C2-C12 alkyl group, C2-C12 haloalkyl group or aryl C1-C6 alkyl group; $R_8$ is hydrogen or cyano group; and $R_9$ is cyano group, carboxylic acid group, C1-C6 alkoxycarbonyl group, aryl group or substituted aryl group), which process comprises reacting a triindole derivative represented by the following general formula (8)

[formula 14]

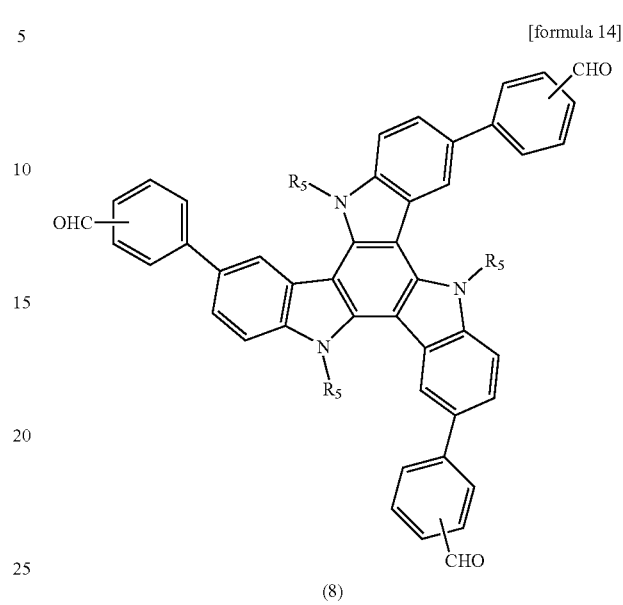

(8)

(wherein $R_5$ has the same definition as given above) with a methylene compound represented by the general formula (9)

[formula 15]

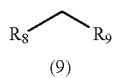

(9)

(wherein $R_8$ and $R_9$ have the same definitions as give above)

[8] A Sym-triindole vinyl derivative represented by the following general formula (11)

[formula 17]

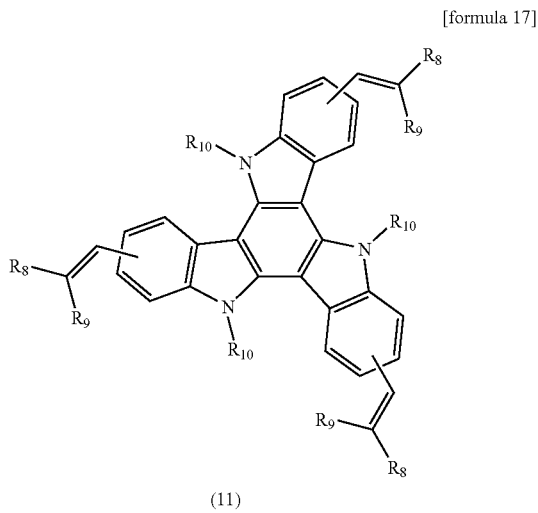

(11)

(wherein $R_8$ is hydrogen or cyano group; $R_9$ is cyano group, carboxylic acid group, C1-C6 alkoxycarbonyl group, aryl group or substituted aryl group; and $R_{10}$ is C2-C12 alkyl group, substituted C2-C12 alkyl group, C2-C12 haloalkyl group or aryl C1-C6 alkyl group).

[9] A process for producing a Sym-triindole derivative represented by the following general formula (11)

[formula 22]

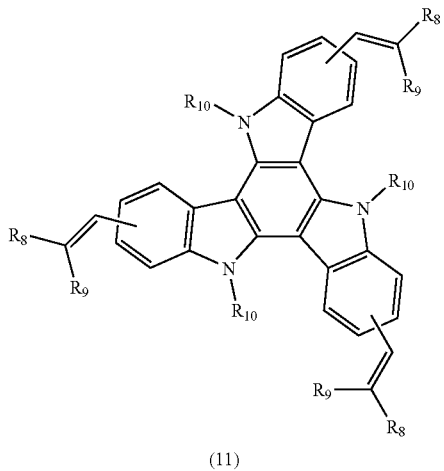

(11)

(wherein $R_8$ is hydrogen or cyano group; $R_9$ is cyano group, carboxylic acid group, C1-C6 alkoxycarbonyl group, aryl group or substituted aryl group; and $R_{10}$ is $C_2$-$C_{12}$ alkyl group, substituted C2-C12 alkyl group, C2-C12 haloalkyl group or aryl C1-C6 alkyl group), which process comprises reacting an oxyindole compound represented by the following general formula (12)

[formula 18]

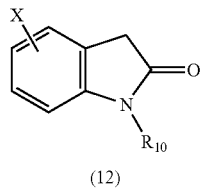

(12)

(wherein $R_{10}$ has the same definition as given above and X is halogen) with a phosphorus oxyhalide to obtain a Sym-halotriindole derivative represented by the following general formula (13)

[formula 19]

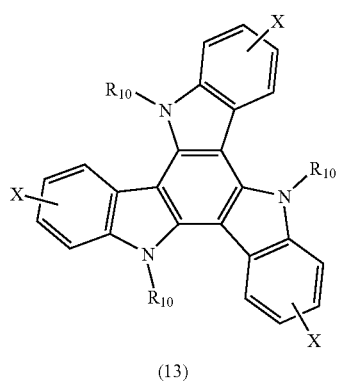

(13)

(wherein $R_{10}$ and X have the same definitions as given above), subjecting it to formylation with a formylating agent in the presence of butyllithium to obtain a Sym-formyltriindole derivative represented by the following general formula (14)

[formula 20]

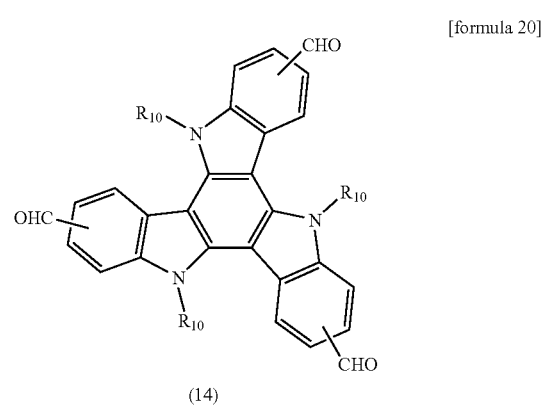

(14)

(wherein $R_{10}$ has the same definition as given above), and reacting it with a methylene compound represented by the following general formula (9)

[formula 21]

(9)

(wherein $R_8$ and $R_9$ have the same definitions as given above).

[10] A process for producing a Sym-triindole derivative represented by the following general formula (11)

[formula 25]

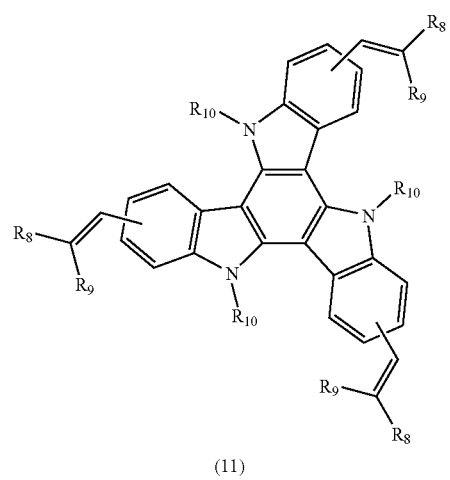

(11)

(wherein $R_8$ is hydrogen or cyano group; $R_9$ is cyano group, carboxylic acid group, C1-C6 alkoxycarbonyl group, aryl group or substituted aryl group; and $R_{10}$ is C2-C12 alkyl group, substituted C2-C12 alkyl group, C2-C12 haloalkyl group or aryl C1-C6 alkyl group), which process comprises reacting a Sym-formyltriindole derivative represented by the following general formula (14)

[formula 23]

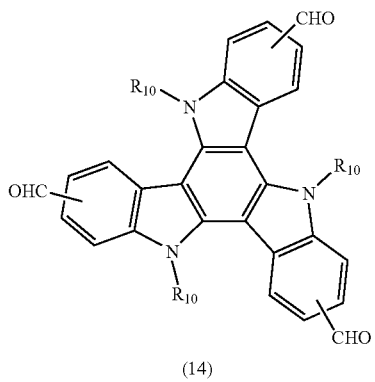

(14)

(wherein $R_{10}$ has the same definition as given above) with a methylene compound represented by the following general formula (9)

[formula 24]

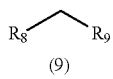

(9)

(wherein $R_8$ and $R_9$ have the same definitions as given above).

[11] A process for producing a Sym-formyltriindole derivative represented by the following general formula (14)

[formula 27]

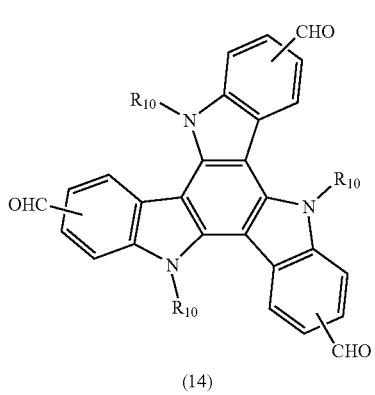

(14)

(wherein $R_{10}$ is C2-C12 alkyl group, C2-C12 substituted alkyl group, C2-C12 haloalkyl group or aryl C1-C6 alkyl group), which process comprises subjecting a Sym-halo-triindole derivative represented by the following general formula (13)

[formula 26]

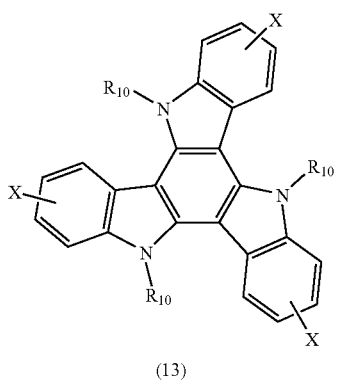

(13)

(wherein $R_{10}$ has the same definition as given above and X is halogen), to formylation with a formylating agent in the presence of butyllithium.

[12] A Sym-triindole derivative represented by the following general formula (15)

[formula 28]

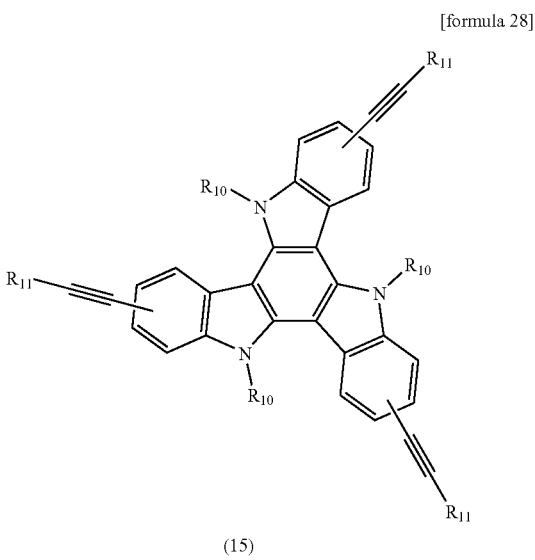

(15)

(wherein $R_{10}$ is C2-C12 alkyl group, C2-C12 substituted alkyl group, C2-C12 haloalkyl group or aryl C1-C6 alkyl group; and $R_{11}$ is aryl group or substituted aryl group).

[13] A process for producing a Sym-triindole derivative represented by the following general formula (15)

[formula 31]

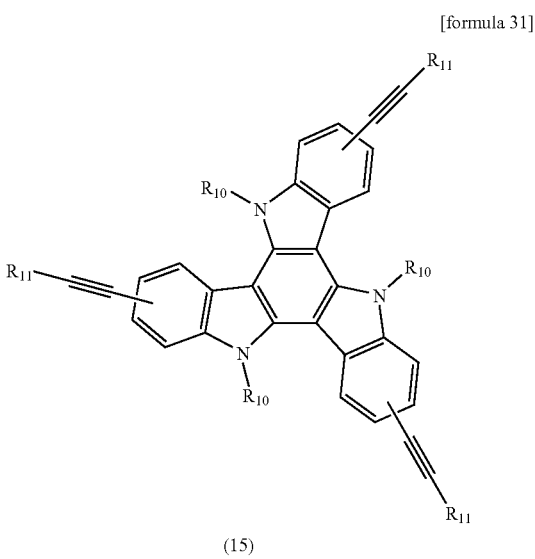

(15)

(wherein $R_{10}$ is C2-C12 alkyl group, substituted C2-C12 alkyl group, C2-C12 haloalkyl group or aryl C1-C6 alkyl group and $R_{11}$ is aryl group or substituted aryl group), which process comprises reacting a Sym-halo-triindole derivative represented by the following general formula (13)

[formula 29]

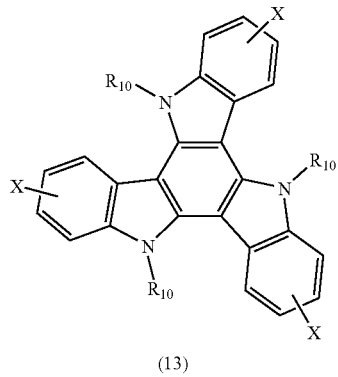

(13)

(wherein $R_{10}$ has the same definition as given above and X is halogen) with an acetylene derivative represented by the following general formula (16)

[formula 30]

  (16)

(wherein $R_1$, has the same definition as given above and $R_{12}$ is hydrogen or trimethylsilyl group).

[14] A Sym-halo-triindole derivative represented by the following general formula (13)

[formula 32]

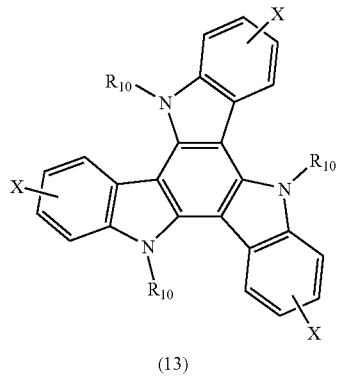

(13)

(wherein $R_{10}$ is C2-C12 alkyl group, substituted C2-C12 alkyl group, C2-C12 haloalkyl group or aryl C1-C6alkyl group; and X is halogen).

Explanation is made on the terms used in the present specification.

The expression of "C1-C6", etc. indicates that the group following the expression has 1 to 6 carbon atoms, in the case of "C1-C6".

"Halogen" indicates fluorine, chlorine, bromine or iodine.

"C1-C6 alkyl group" indicates straight chain or branched chain C1-C6 alkyl group having 1 to 6 carbon atoms and, as specific examples thereof, there can be mentioned methyl group, ethyl group, n-propyl group, isopropyl group, n-butyl group, isobutyl group, sec-butyl group, tert-butyl group, n-pentyl group, n-hexyl group and 3,3-dimethylbutyl group.

"C2-C12 alkyl group" indicates straight chain or branched chain C2-C12 alkyl group having 2 to 12 carbon atoms and, as specific examples thereof, there can be mentioned ethyl group, n-propyl group, isopropyl group, n-butyl group, isobutyl group, sec-butyl group, tert-butyl group, n-pentyl group, n-hexyl group, 3,3-dimethylbutyl group, n-heptyl group, n-octyl group, 2-ethylhexyl group, n-decyl group and n-dodecyl group.

"Aryl group" indicates aromatic group which may contain heterocyclic atom and which is a 5- or 6-membered single ring or a condensed ring formed by any condensation of 5-membered rings and/or 6-membered rings. There can be mentioned, for example, aromatic hydrocarbon groups of single ring or condensed ring, such as phenyl group, 1-naphthyl group, 2-naphthyl group, 1-anthranyl group, 2-anthranyl group, 9-anthranyl group, 1-phenathryl group, 2-phenanthryl group, 9-phenanthryl group, 3-phenanthryl group, 4-phenathryl, 1-pyrenyl group, 2-pyrenyl group, 4-pyrenyl group and the like; and aromatic heterocyclic ring group of single ring or condensed ring containing at least one nitrogen, oxygen or sulfur as heterocyclic atom, such as 2-pyridyl group, 3-pyridyl group, pyrrolyl group, pyrazolyl group, triazolyl group, quinolinyl group, indolyl group, isoindolyl group, thienyl group, benzothienyl group, furyl group, benzofuryl group, thiazolyl group, oxadiazolyl group, benzothiazolyl group, oxazolyl group, isoxazolyl group, benzoxazolyl group, thiadiazolyl group, benzothiadiazolyl group and the like.

"Substituted aryl group" indicates aryl group having the above-shown meaning, substituted independently with 1 to 7 groups selected from halogen having the above-mentioned meaning, cyano group, formyl group and aryl group. There can be mentioned, for example, 2-chlorophenyl group, 4-cyanophenyl group, 4-formylphenyl group, 2-phenyl-1,3,4-oxadiazol-5-yl group, 2-(4-n-butylphenyl)-1,3,4-oxadiazol-5-yl group, 2-(4-tert-butylphenyl)-1,3,4-oxadiazol-5-yl group, and 2-(4-n-hexylphenyl)-1,3,4-oxadiazol-5-yl group.

"C1-C6 alkoxy group" indicates "(C1-C6 alkyl having the above-shown meaning)-O— group". There can be mentioned, for example, methoxy group, ethoxy group, n-propoxy group, isopropoxy group, n-butoxy group, tert-butoxy group,n-pentyloxy group and n-hexyloxy group.

"C1-C6 alkoxycarbonyl group" indicates "(C1-C6 alkoxy having the above-shown meaning)-CO— group". There can be mentioned, for example, methoxycarbonyl group and ethoxycarbonyl group.

"Aryloxy group" indicates "(aryl having the above-shown meaning)-O— group". There can be mentioned, for example, henoxy group.

"C1-C6 haloalkyl group" indicates straight chain or branched chain C1-C6 alkyl group substituted with 1 to 25 same or different halogens having the above-shown meaning. There can be mentioned, for example, chloromethyl group, dichloromethyl group, trichloromethyl group and trifluoromethyl group.

"C2-C12 haloalkyl group" indicates straight chain or branched chain C2-C12 alkyl group substituted with 1 to 13 same or different halogens having the above-shown meaning. There can be mentioned, for example, chloroethyl group, 1,1-dichloroethyl group, 2,2,2-trichloroethyl group and 2,2,2-trifluoroethyl group.

"Substituted C1-C6 alkyl group" indicates straight chain or branched chain C1-C6 alkyl group substituted with 1 to 13 same or different hydroxy groups, C1-C6 alkoxy groups having the above-shown meaning and aryl groups having the above-shown meaning. There can be mentioned, for example, hydroxymethyl group, methoxymethyl group and phenylethyl group.

"Substituted C2-C12 alkyl group" indicates straight chain or branched chain C2-C12 alkyl group substituted with 1 to 13 same or different hydroxy groups having the above-shown meaning and C1-C6 alkoxy groups having the above-shown meaning. There can be mentioned, for example, hydroxyethyl group and methoxyethyl group.

"Aryl C1-C6 alkyl group" indicates straight chain or branched chain C1-C6 alkyl group substituted with 1 to 13 same or different aryl groups having the above-shown meaning. There can be mentioned, for example, benzyl group and phenylethyl group.

"C2-C6 alkenyl group" indicates straight chain or branched chain C2-C6 alkenyl group. There can be mentioned, for example, vinyl group, 1-propenyl group and 1-butenyl group.

"Carboxyl group" indicates carboxyl group or carboxyl group of salt form. There can be mentioned, for example, groups such as carboxylic acid (—COOH), sodium carboxylate (—COONa), potassium carboxylate (—COOK), lithium carboxylate (—COOLi), pyridinium carboxylate (—COO-H.pyridine) and the like.

"Substituted C2-C6 alkenyl group" indicates straight chain or branched chain C2-C6 alkenyl group substituted with 1 to 11 same or different cyano groups having the above-shown meaning, carboxylic acid groups having the above-shown meaning, C1-C6 alkoxycarbonyl groups having the above-shown meaning, aryl groups having the above-shown meaning, and substituted aryl groups having the above-shown meaning. There can be mentioned, for example, 2,2-dicyanovinyl group, (2-cyano-2-ethoxycarbonyl)vinyl group, (2-cyano-2-carboxy)vinyl group, (2-cyano-2-phenyl)vinyl group, (2-cyano-2-(4-nitrophenyl))vinyl group, and (2-cyano-2-(4-pyridyl))vinyl group.

"C2-C6 alkynyl group" indicates straight chain or branched chain C2-C6 alkynyl group. There can be mentioned, for example, ethynyl group, 1-propynyl group and 1-butynyl.

"Substituted C2-C6 alkynyl group" indicates straight chain or branched chain C2-C6 alkynyl group substituted with 1 to 9 aryl groups having the above-shown meaning. There can be mentioned, for example, phenylethynyl group and (4-pyridyl) ethynyl group.

"Acyl group" indicates "(C1-C6 alkyl having the above-shown meaning)-CO— group", "C1-C6 haloalkyl group having the above-shown meaning)-CO group, "aryl group having the above-shown meaning)-CO— group", or "substituted aryl group having the above-shown meaning)-CO— group". There can be mentioned, for example, acetyl group, propionyl group and benzoyl group.

"Mono-substituted amino group" indicates amino group mono-substituted with a C1-C6 alkyl group having the above-shown meaning or with an aryl group having the above-shown meaning. There can be mentioned, for example, methylamino group, ethylamino group and phenylamino group.

"Di-substituted amino group" indicates amino group di-substituted with same or different C1-C6 alkyl groups having the above-shown meaning or same or different aryl groups having the above-shown meaning. There can be mentioned, for example, dimethylamino group, diethylamino group and diphenylamino group.

"Acylamino group" indicates amino group mono-substituted with a C1-C6 acyl group having the above-shown meaning. There can be mentioned, for example, acetylamino group, propionylamino group and butyrylamino group.

"C1-C6 alkylsulfenyl group" indicates "(C1-C6 alkyl having the above-shown meaning)-S— group". There can be mentioned, for example, methylsulfenyl group (methylthio group) and ethylsulfenyl group (ethylthio group).

"Arylsulfenyl group" indicates "(aryl having the above-shown meaning)-S— group". There can be mentioned, for example, phenylsulfenyl group (phenylthio group).

"Substituted arylsulfenyl group" indicates "(substituted aryl group having the above-shown meaning)-S— group". There can be mentioned, for example, (4-chlorophenyl)sulfenyl group ((4-chlorophenyl)thio group).

"C1-C6 haloalkylsulfenyl group" indicates "(C1-C6 haloalkyl having the above-shown meaning)-S— group". There can be mentioned, for example, trifluoromethylsulfenyl group (trifluoromethylthio group).

"Aralkylsulfenyl group" indicates "(aryl having the above-shown meaning)-(alkyl having the above-shown meaning)-S— group" or "(substituted aryl having the above-shown meaning)-(alkyl having the above-shown meaning)-S— group". There can be mentioned, for example, benzylsulfenyl group (benzylthio group), (4-chlorobenzyl)sulfenyl group ((4-chlorobenzyl)thio group).

"C1-C6 alkylsulfinyl group" indicates "(C1-C6 alkyl having the above-shown meaning)-SO— group". There can be mentioned, for example, methylsulfinyl group and ethylsulfinyl group.

"C1-C6 haloalkylsulfinyl group" indicates "(C1-C6 haloalkyl having the above-shown meaning)-SO— group".

There can be mentioned, for example, trifluoromethylsulfinyl group, chloromethylsulfinyl group and 2-chloroethylsulfinyl group.

"Arylsulfinyl group" indicates "(aryl having the above-shown meaning)-SO— group". There can be mentioned, for example, phenylsulfinyl group.

"Substituted arylsulfinyl group" indicates "(substituted aryl having the above-shown meaning)-SO— group". There can be mentioned, for example, 4-chlorophenylsulfinyl group.

"C1-C6 alkylsulfonyl group" indicates "(C1-C6 alkyl having the above-shown meaning)-$SO_2$— group". There can be mentioned, for example, methanesulfonyl group and ethanesulfonyl group.

"C1-C6 haloalkylsulfonyl group" indicates "(C1-C6 haloalkyl having the above-shown meaning)-$SO_2$— group". There can be mentioned, for example, trifluoromethanesulfonyl group, chloromethanesulfonyl group and 2-chloroethanesulfonyl group.

"Arylsulfonyl group" indicates "(aryl having the above-shown meaning)-$SO_2$— group". There can be mentioned, for example, phenylsulfonyl group.

"Substituted arylsulfonyl group" indicates "(substituted aryl having the above-shown meaning)-$SO_2$— group". There can be mentioned, for example, (4-chlorophenyl)sulfonyl group.

"Sulfonic acid group" indicates —$SO_2$—OH group.

"N-mono-substituted carbamoyl group" indicates carbamoyl group whose nitrogen atom is mono-substituted with a C1-C6 alkyl group having the above-shown meaning or with an aryl group having the above-shown meaning. There can be mentioned, for example, methylcarbamoyl group and phenylcarbamoyl group.

"N,N-di-substituted carbamoyl group" indicates carbamoyl group whose nitrogen atom is di-substituted with C1-C6 alkyl groups having the above-shown meaning or with aryl groups having the above-shown meaning. There can be mentioned, for example, dimethylcarbamoyl group and diphenylcarbamoyl group.

"Hydrazonomethyl group" indicates —CH=N—$NH_2$ group.

"N-mono-substituted hydrazonomethyl group" indicates hydrazonomethyl group whose nitrogen atom is mono-substituted with a C1-C6 alkyl group having the above-shown meaning or with an aryl group having the above-shown meaning. There can be mentioned, for example, methylhydrazonomethyl group and phenylhydrazonomethyl group.

"N,N-di-substituted hydrazonomethyl group" indicates hydrazonomethyl group whose nitrogen atom is di-substituted with C1-C6 alkyl groups having the above-shown meaning or with aryl groups having the above-shown meaning. There can be mentioned, for example, dimethylhydrazonomethyl group and diphenylhydrazonomethyl group.

"Oximemethyl group (hydroxyiminomethyl group)" indicates —CH=N—OH group. "C1-C6 alkoxyiminomethyl group" indicates oxyiminomethyl group whose oxygen atom is substituted with C1-C6 alkyl group having the above-shown meaning, and there can be mentioned, for example, methoxyiminomethyl group and ethoxyiminomethyl group.

"Aryloxyiminomethyl group" indicates oxyiminomethyl group whose oxygen atom is substituted with aryl group having the above-shown meaning. There can be mentioned, for example, phenoxyiminomethyl group.

The present invention is described in detail below.

The present invention [1] lies in a Sym-triindole derivative represented by the general formula (1). In the general formula (1), $R_1$, $R_2$, $R_3$ and $R_4$ may be the same or different from each other and are each independently hydrogen, halogen, $C_1$-$C_6$ alkyl group, $C_1$-$C_6$ haloalkyl group, substituted $C_1$-$C_6$ alkyl group, $C_2$-$C_6$ alkenyl group, substituted $C_2$-$C_6$ alkenyl group, C2-C6 alkynyl group, substituted C2-C6 alkynyl group, hydroxyl group, $C_1$-$C_6$ alkoxy group, aryloxy group, amino group, mono-substituted amino group, di-substituted amino group, acylamino group, mercapto group, $C_1$-$C_6$ alkylsulfenyl group, $C_1$-$C_6$ haloalkylsulfenyl group, arylsulfenyl group, substituted arylsulfenyl group, $C_1$-$C_6$ alkylsulfinyl group, $C_1$-$C_6$ haloalkylsulfinyl group, aralkylsulfenyl group, arylsulfinyl group, substituted arylsulfinyl group, $C_1$-$C_6$ alkylsulfonyl group, $C_1$-$C_6$ haloalkylsulfonyl group, arylsulfonyl group, substituted arylsulfonyl group, sulfonic acid group (hydroxysulfonyl group), aryl group, substituted aryl group, cyano group, nitro group, formyl group, acyl group, carboxyl group, $C_1$-$C_6$ alkoxycarbonyl group, carbamoyl group, N-mono-substituted carbamoyl group, N,N-di-substituted carbamoyl group, hydrazonomethyl group (—CH=N—$NH_2$ group), N-mono-substituted hydrazonomethyl group, N,N-di-substituted hydrazonomethyl group, oximemethyl group (hydroxyiminomethyl group), $C_1$-$C_6$ alkoxyiminomethyl group, or aryloxyiminomethyl group; $R_5$ is $C_2$-$C_{12}$ alkyl group, substituted $C_2$-$C_{12}$ alkyl group, $C_2$-$C_{12}$ haloalkyl group, or aryl $C_1$-$C_6$ alkyl group; in no event, all of $R_1$, $R_2$, $R_3$ and $R_4$ are hydrogen simultaneously.

Therefore, as examples of the compound of the present invention [1], there can be mentioned compounds shown in Table 1. Incidentally, the abbreviations used in each of the following Tables have the following meanings.

MeO: methoxy group

COOMe: methoxycarbonyl group

COOEt: ethoxycarbonyl

Ph: phenyl group

NHBn: benzylamino group

SPh: phenylsulfenyl group (phenylthio group)

SOPh: phenylsulfinyl group $SO_2$Ph: phenylsulfonyl group

COMe: acetyl group

CONHPh: phenylcarbamoyl group

NHCOPh: benzoylamino group vinyl: vinyl group

Et: ethyl group n-Pr: n-propyl group

Bu: n-butyl group

Pen: n-pentyl group n-Hex: n-hexyl group (2-Et)Hex: 2-ethylhexyl group dicyanovinyl: 2,2-dicyanovinyl group Py: pyridyl group TMS-Ethynyl: trimethylsilylethynyl group

TABLE 1

[Formula 33]

| Compound No. | $R_1$ | $R_2$ | $R_3$ | $R_4$ | $R_5$ | Melting point (° C.) |
|---|---|---|---|---|---|---|
| 1 | Br | H | H | H | Et | |
| 2 | H | Br | H | H | n-Pr | |
| 3 | H | H | Br | H | Bu | |
| 4 | H | H | H | Br | Penthyl | |
| 5 | H | H | Br | H | n-Hex | 205-207 |
| 6 | H | H | Br | H | (2-Et)Hex | 161 |
| 7 | H | H | Me | H | n-Hex | 160 |
| 8 | H | H | CHO | H | n-Hex | 185-187 |
| 9 | H | H | CHO | H | (2-Et)Hex | 243 |
| 10 | H | H | CN | H | n-Hex | |
| 11 | H | H | COOMe | H | n-Hex | |
| 12 | H | COOH | H | H | n-Hex | |
| 13 | H | MeO | H | H | n-Hex | |
| 14 | H | H | $NH_2$ | H | n-Hex | |
| 15 | H | H | NHBn | H | n-Hex | |
| 16 | H | H | SPh | H | n-Hex | |
| 17 | H | H | SOPh | H | n-Hex | |
| 18 | H | H | $SO_2Ph$ | H | n-Hex | |
| 19 | H | H | $SO_3H$ | H | n-Hex | |
| 20 | H | H | COMe | H | n-Hex | |
| 21 | H | H | $CONH_2$ | H | n-Hex | |
| 22 | H | H | CONHPh | H | n-Hex | |
| 23 | H | H | NHCOPh | H | n-Hex | |
| 24 | H | H | $NO_2$ | H | n-Hex | |
| 25 | H | H | $CF_3$ | H | n-Hex | |
| 26 | H | H | Br | H | CF3CH2 | |
| 27 | H | H | TMS-Ethynyl | H | n-Hex | |
| 28 | H | H | Vinyl | H | n-Hex | |
| 29 | H | H | CN | H | (2-Et)Hex | 248 |

The present invention [2] lies in a process for producing a substituted Sym-triindole derivative represented by the general formula (1), which comprises reacting an oxyindole represented by the general formula (2) with a phosphorus oxyhalide.

Firstly, description is made on the oxyindole represented by the general formula (2), used as a raw material of the present invention.

In the general formula (2), $R_1$, $R_2$, $R_3$ and $R_4$ may be the same or different from each other and are each independently hydrogen, halogen, $C_1$-$C_6$ alkyl group, $C_1$-$C_6$ haloalkyl group, substituted $C_1$-$C_6$ alkyl group, $C_2$-$C_6$ alkenyl group, substituted $C_2$-$C_6$ alkenyl group, C2-C6 alkynyl group, substituted C2-C6 alkynyl group, hydroxyl group, $C_1$-$C_6$ alkoxy group, aryloxy group, amino group, mono-substituted amino group, di-substituted amino group, acylamino group, mercapto group, $C_1$-$C_6$ alkylsulfenyl group, $C_1$-$C_6$ haloalkylsulfenyl group, aralkylsulfenyl group, arylsulfenyl group, substituted arylsulfenyl group, $C_1$-$C_6$ alkylsulfinyl group, C1-C6 haloalkylsulfinyl group, arylsulfinyl group, substituted arylsulfinyl group, $C_1$-$C_6$ alkylsulfonyl group, $C_1$-$C_6$ haloalkylsulfonyl group, arylsulfonyl group, substituted arylsulfonyl group, sulfonic acid group (hydroxysulfonyl group), aryl group, substituted aryl group, cyano group, nitro group, formyl group, acyl group, carboxyl group, $C_1$-$C_6$ alkoxycarbonyl group, carbamoyl group, N-mono-substituted carbamoyl group, N,N-di-substituted carbamoyl group, hydrazonomethyl group (—CH=N—$NH_2$ group), N-monosubstituted hydrazonomethyl group, N,N-di-substituted hydrazonomethyl group, oximemethyl group (hydroxyiminomethyl group), $C_1$-$C_6$ alkoxyiminomethyl group, or aryloxyiminomethyl group; $R_5$ is $C_2$-$C_{12}$ alkyl group, substituted $C_2$-$C_{12}$ alkyl group, $C_2$-$C_{12}$ haloalkyl group, or aryl $C_1$-$C_6$ alkyl group; in no event, all of $R_1$, $R_2$, $R_3$ and $R_4$ are hydrogen simultaneously.

In the general formula (2), bromine is preferred as each halogen as $R_1$ to $R_4$, from the standpoints of reactivity and commercial availability; and C2-12 alkyl group, particularly n-hexyl group or 2-ethylhexyl group is preferred as $R_5$.

Therefore, there can be mentioned, as specific examples of the oxyindole usable in the above reaction, N-ethyl-5-bromooxyindole, N-ethyl-6-bromooxyindole, N-ethyl-7-bromooxyindole, N-ethyl-5,6-dibromooxyindole, N-ethyl-5,7-dibromooxyindole, N-ethyl-5-chlorooxyindole, N-ethyl-5-iodooxyindole, N-propyl-5-bromooxyindole, N-isopropyl-5-bromooxyindole, N-(n-hexyl)-5-bromooxyindole, N-(n-octyl)-5-bromooxyindole, N-(2-ethyl)hexyl-5-bromooxyindole, and N-(n-hexyl)-5-methyloxyindole.

The oxyindole used in the present invention is known, or can be produced by reacting a corresponding aniline with chloroacetyl chloride in the presence of aluminum chloride.

As the phosphorus oxyhalide, there can be mentioned, for example, phosphorus oxychloride and phosphorus oxybromide. Ordinarily, phosphorus oxychloride is used preferably.

The molar ratio of the oxyindole used as a raw material and the phosphorus oxyhalide may be any molar ratio as long as stirring is possible. However, the phosphorus oxyhalide is used in an amount of, for example, preferably 0.5 to 30 liters, more preferably 1 to 10 liters relative to 1 mole of the oxyindole as raw material.

The temperature of the reaction is not particularly restricted as long as the reaction proceeds at the temperature, but is preferred to be, for example, a range from 80° C. to the reflux temperature.

The period of the reaction is not particularly restricted but is preferred to be, for example, 1 to 48 hours.

Incidentally, a compound wherein $R_1$, $R_2$, $R_3$ and $R_4$ are hydrazonomethyl group, N-mono-substituted hydrazonomethyl group or N,N-di-substituted hydrazonomethyl group, can be produced by reacting a compound (obtained as above) wherein $R_1$, $R_2$, $R_3$ and $R_4$ are each formyl group, with hydrazine, an N-mono-substituted hydrazine [typified by a C1-C6 alkylhydrazine (e.g. methylhydrazine or ethylhydrazine) or phenylhydrazine], or an N,N-di-substituted hydrazine [typified by a di(C1-C6 alkyl)hydrazine (e.g. N,N-dimethylhydrazine or N,N-diethylhydrazine) or diphenylhydrazine].

Also, a compound wherein $R_1$, $R_2$, $R_3$ and $R_4$ are oximemethyl group (hydroxyiminomethyl group) or O-substituted oxyiminomethyl group (e.g. C1-C6 alkoxyiminomethyl group or aryloxyiminomethyl group), can be produced by reacting a compound (obtained as above) wherein $R_1$, $R_2$, $R_3$ and $R_4$ are each formyl group, with hydroxylamine or a salt thereof, or by reacting a compound (obtained as above) wherein $R_1$, $R_2$, $R_3$ and $R_4$ are each formyl group, with an O-substituted oxyamine such as C1-C6 alkoxyamine (alkanolamine) [e.g. methoxyamine (methanolamine) or salt thereof, or ethoxyamine (ethanolamine) of salt thereof], aryloxyamine (typified by phenoxyamine), or the like.

The present invention [3] lies in a Sym-triindole derivative represented by the general formula (3). In the general formula (3), $R_6$ is hydrogen atom; formyl group; cyano group; dicyanovinyl group; C1-C6 alkoxycarbonyl group such as methoxycarbonyl group, ethoxycarbonyl group, propoxycarbonyl group or the like; aryl group such as oxadiazolyl group or the like; or substituted aryl group such as 2-chlorophenyl group, 4-cyanophenyl group, 4-formylphenyl group, 2-phenyl-1,3,4-oxadiazol-5-yl group, 2-(4-n-butylphenyl)-1,3,4-oxadiazol-5-yl group, 2-(4-tert-butylphenyl)-1,3,4-oxadiazol-5-yl group, 2-(4-n-hexylphenyl)-1,3,4-oxadiazol-5-yl group or the like.

Therefore, compounds shown in Table 2 can be mentioned as examples of the compound of the present invention.

TABLE 2

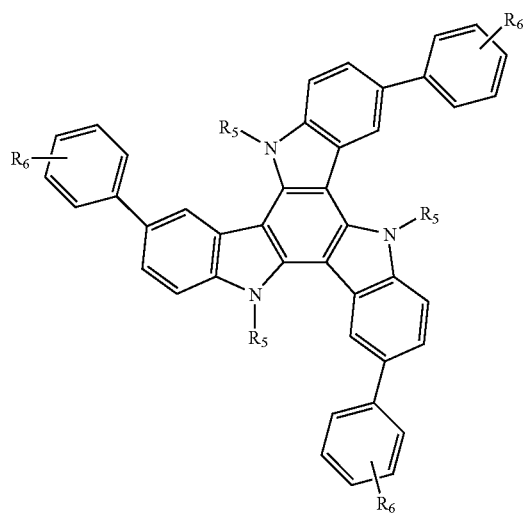

[Formula 34]

| Compound No. | $R_5$ (each of three $R_5$s) | $R_6$ (each of three $R_6$s) | Melting point(° C.) |
|---|---|---|---|
| 30 | n-Hex | H | |
| 31 | n-Hex | 4-CHO | 245-257 |
| 32 | n-Hex | 4-COOEt | 203-213 |
| 33 | n-Hex | 4-CN | 297-303 |
| 34 | n-Hex | 4-dicyanovinyl | 281-291 |
| 35 | n-Hex | 2-CHO | |
| 36 | n-Hex | 3-CHO | |
| 37 | n-Hex | 2-CN | |
| 38 | n-Hex | 3-CN | |
| 39 | (2-Et)Hex | ![oxadiazole-phenyl] | |
| 40 | (2-Et)Hex | ![oxadiazole-phenyl-n-C4H9] | |
| 41 | (2-Et)Hex | ![oxadiazole-phenyl-tBu] | |

TABLE 2-continued

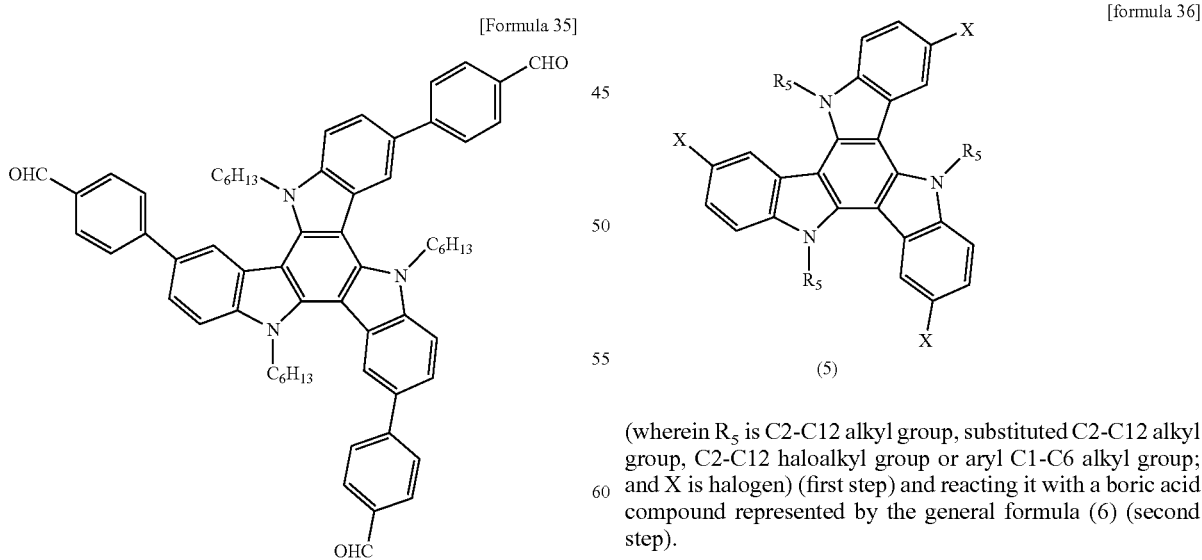

[Formula 34]

| Compound No. | $R_5$ (each of three $R_5$s) | $R_6$ (each of three $R_6$s) | Melting point(° C.) |
|---|---|---|---|
| 42 | (2-Et)Hex | ![oxadiazole-phenyl-n-C6H13] | |

Figure 2:
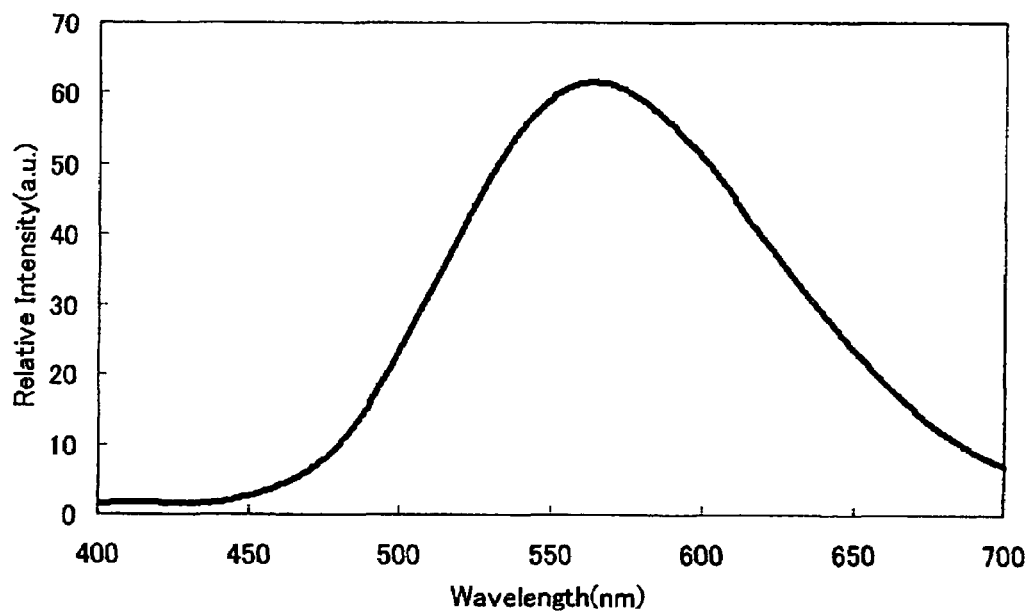
FIG. 2 is a fluorescent spectrum of Sym-N-(n-hexyl)-5-(4-formylphenyl)triindole (formula 36) in a dichloromethane solution state.
Figure 3:
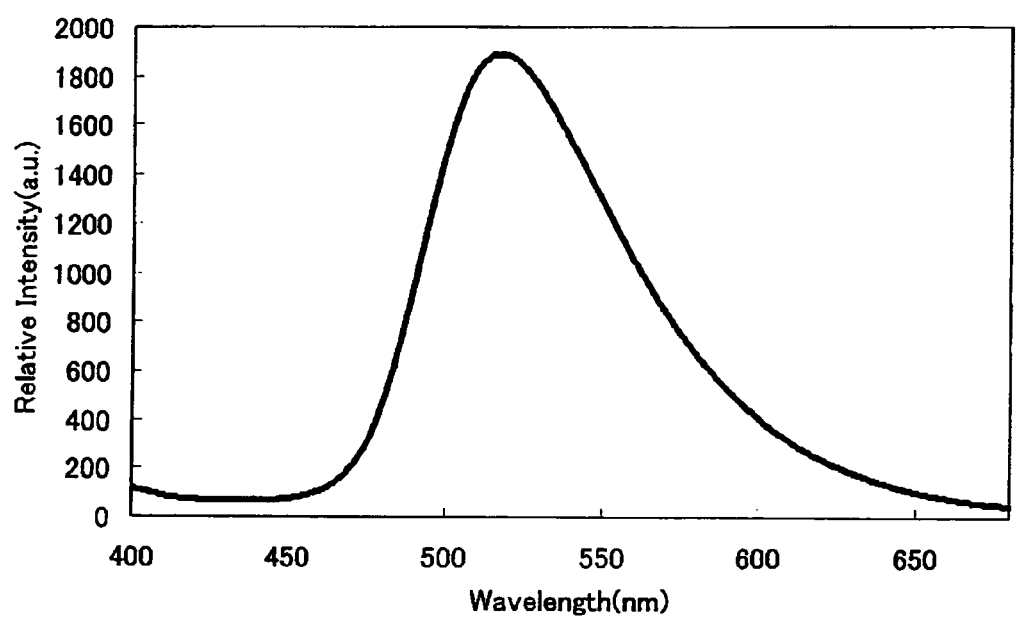
FIG. 3 is a fluorescent spectrum of Sym-N-(n-hexyl)-5-(4-formylphenyl)triindole (formula 36) in a solid state.

As to Sym-N-(n-hexyl)-5-(4-formylphenyl)triindole (formula 35) which is a representative compound of the present invention, there are shown its absorption spectrum in a visible to ultraviolet region, in FIG. 1, and its fluorescent spectra in FIG. 2 (as measured in a dichloromethane solution) and FIG. 3 (as measured in a solid state).

[Formula 35]

The compound obtained by the present invention has a fluorescent spectrum from 400 nm to around 700 nm and accordingly it is expected that the compound is usable in organic EL materials, solar cells, etc.

The present invention [4] lies in a process for producing a Sym-triindole derivative represented by the general formula (7), which comprises reacting an N-substituted-5-halo-oxyindole represented by the general formula (4) with a phosphorus oxyhalide to obtain an N-substituted-5-halo-triindole represented by the following general formula (5)

[formula 36]

(5)

(wherein $R_5$ is C2-C12 alkyl group, substituted C2-C12 alkyl group, C2-C12 haloalkyl group or aryl C1-C6 alkyl group; and X is halogen) (first step) and reacting it with a boric acid compound represented by the general formula (6) (second step).

Firstly, the first step of the present invention is described. The present step is a step for reacting an N-substituted-5-halo-oxyindole represented by the general formula (4) with a phosphorus oxyhalide to produce an N-substituted-5-halo-triindole.

The molar ratio of the N-substituted-5-halo-oxyindole represented by the general formula (4) and the phosphorus oxyhalide both used as raw materials in the present step may be any molar ratio as long as stirring is possible. However, the amount of the phosphorus oxyhalide is preferably 0.5 to 30 liters, more preferably 1 to 10 liters relative to 1 mole of the oxyindole.

The temperature of the reaction is not particularly restricted as long as the reaction proceeds at the temperature, but is preferred to be, for example, a range from 80° C. to the reflux temperature.

The period of the reaction is not particularly restricted but is preferred to be, for example, 1 to 48 hours.

Then, the second step is described. The present step is a step for reacting the N-substituted-5-halo-oxyindole obtained in the previous step, with a boric acid compound represented by the general formula (6) to produce a Sym-triindole derivative represented by the general formula (7).

The boric acid compound represented by the general formula (6) (which is a raw material in the present step) is explained. In the general formula (6), $R_6$ is hydrogen atom, formyl group, cyano group, or C1-C6 alkoxycarbonyl group such as methoxycarbonyl, ethoxycarbonyl, n-propoxycarbonyl, isopropoxycarbonyl or the like; and $R_a$ and $R_b$ are each independently hydrogen atom, C1-C6 alkyl group, or optionally substituted phenyl and may be combined to each other to form a ring. (Therefore, $R_aO—B—OR_b$ indicates formic acid group; straight chain or branched chain C1-C12 alkyl borate such as methoxyboric acid, ethoxyboric acid, isopropoxyboric acid or the like; or cyclic boric acid ester such as 4,4,5,5-tetramethyl-1,3,2-dioxaborolane-2-yl, 5,5-dimethyl-1,3,2-dioxaborinane-2-yl or the like.

Therefore, as specific examples of the boric acid compound represented by the general formula (6), usable in the second step reaction, there can be mentioned phenylboric acid, methyl phenylborate, ethyl phenylborate, isopropyl phenylborate, 2-formylphenylboric acid, 3-formylphenylboric acid, 4-formylphenylboric acid, methyl 4-(4,4,5,5-tetramethyl-1,3,2-dioxaborolane-2-yl)benzoate, ethyl 4-(4,4,5,5-tetramethyl-1,3,2-dioxaborolane-2-yl)benzoate, 4-(4,4,5,5-tetramethyl-1,3,2-dioxaborolane-2-yl)benzonitrile, and 4-(5,5-dimethyl-1,3,2-dioxaborinane-2-yl)benzaldehyde.

In the reaction of the second step, the molar ratio of the boric acid compound represented by the general formula (6) and the N-substituted-5-halo-triindole derivative may be any molar ratio; however, the preferred amount of the former is, for example, 3 to 15 moles relative to 1 mole of the N-substituted-5-halo-triindole derivative.

The reaction is conducted using a solvent. As to the solvent usable therein, there is no restriction as long as the solvent does no impair the present reaction. There are preferably used, for example, aromatic hydrocarbons such as benzene, toluene, xylene and the like; aprotic polar solvents such as dimethylformamide, diethylformamide, dimethylacetamide and the like; cyclic ethers such as tetrahydrofuran (THF), dioxane and the like; chain ethers such as monoglyme, diglyme and the like; alcohols such as methanol, ethanol, butanol, ethylene glycol, propylene glycol, PEG-400 and the like; and water.

The solvent used in the reaction may be a single solvent or a mixed solvent of any mixing ratio.

The amount of the solvent used in the reaction may be any as long as stirring is possible; however, it is preferred to be, for example, 0.1 to 10 liters relative to 1 mole of the Sym-N-substituted-5-halo-triindole (a raw material).

The temperature of the reaction is not particularly restricted as long as the reaction proceeds at the temperature, but is preferred to be, for example, 40° C. to the reflux temperature of the solvent used. The period of the reaction is not particularly restricted but is, for example, 0.5 to 48 hours.

The invention [5] is the second step of the invention [4] described above.

The invention [6] is the first step of the invention [4] described above.

The invention [7] lies in a process for producing a Sym-triindole derivative represented by the general formula (10), which comprises reacting a Sym-triindole derivative represented by the general formula (8) with a methylene compound represented by the general formula (9).

In the methylene compound represented by the general formula (9), used in the reaction of the invention [7], $R_8$ is hydrogen atom or cyano group; and $R_9$ is cyano group, carboxylic acid group (e.g. carboxylic acid, sodium carboxylate, potassium carboxylate, lithium carboxylate or pyridinium carboxylate), C1-C6 alkoxycarbonyl group (e.g. methoxycarbonyl or ethoxycarbonyl), aryloxycarbonyl group (e.g. phenoxycarbonyl group), aryl group (e.g. phenyl group, naphthyl group, 2-pyridyl group, 3-pyridyl group, 4-pyridyl group, 2-pyrimidine group, 4-pyrimidine group or triazine group), or substituted aryl group (e.g. 2-nitrophenyl group, 3-nitrophenyl group, 4-nitrophenyl group, 4-formylphenyl group, 4-cyanophenyl group or 6-methyl-2-pyridine group). The substituted aryl group of $R_9$ includes a salt thereof when the group is a heterocyclic ring containing nitrogen as heterocyclic atom.

Therefore, as the methylene compound represented by the general formula (9), usable in the reaction of the invention [7], there can be mentioned, for example, acetonitrile, malononitrile, methyl acetate, ethyl acetate, cyanoacetic acid, methyl cyanoacetate, ethyl cyanoacetate, phenyl cyanoacetate, 4-nitrophenyl cyanoacetate, 2-cyanomethylpyridine, 3-cyanomethylpyridine, 4-cyanomethylpyridine, 2-cyanomethylpyrimidine, benzyl cyanide and 4-nitrobenzyl cyanide.

The molar ratio of the methylene compound represented by the general formula (9), usable in the reaction of the invention [7] may be any molar ratio as long as the reaction is not impaired. However, the amount of the methylene compound is 0.1 to 30 moles, preferably 1 to 10 moles relative to 1 mole of the Sym-triindole derivative represented by the general formula (8).

The reaction is ordinarily conducted using a solvent. As the solvent used in the reaction, there can be mentioned, for example, aprotic polar solvents such as dimethylformamide, dimethylacetamide, diethylacetamide, N-methylpyrrolidone, N,N-dimethylimidazolinone, tetramethylurea and the like; aromatic hydrocarbons such as toluene, xylene, chlorobenzene and the like; chain or cyclic ethers such as diethyl ether, diisopropyl ether, tetrahydrofuran, dioxane and the like; acetic acid esters such as methyl acetate, ethyl acetate, butyl acetate and the like; and nitrites such as acetonitrile and the like. The solvent used in the reaction may be a single solvent or a mixed solvent of any mixing ratio.

The amount of the solvent used in the reaction may be any as long as stirring is possible. However, the preferred amount is, for example, 0.1 to 30 liters, preferably 0.5 to 10 liters relative to 1 mole of the Sym-triindole derivative of the general formula (8) which is a raw material.

The temperature of the reaction may be any temperature as long as the reaction proceeds at the temperature, but is preferred to be, for example, −20° C. to the reflux temperature of the solvent used.

The period of the reaction is not particularly restricted but is preferred to be, for example, 1 to 48 hours.

The invention [8] lies in a Sym-vinyltriindole derivative represented by the general formula (11). In the general formula (11), $R_8$ is hydrogen atom or cyano group; and $R_9$ is cyano group, carboxylic acid group (e.g. carboxylic acid, sodium carboxylate, potassium carboxylate, lithium carboxylate or pyridinium carboxylate), C1-C6 alkoxycarbonyl group (e.g. methoxycarbonyl or ethoxycarbonyl), aryloxycarbonyl group (e.g. phenoxycarbonyl), aryl group (e.g. phenyl group, naphthyl group, 2-pyridyl group, 3-pyridyl group, 4-pyridyl group, 2-pyrimidine group, 4-pyrimidine group or triazine group), or substituted aryl group (e.g. 2-nitrophenyl group, 3-nitrophenyl group, 4-nitrophenyl group, 4-formylphenyl group, 4-cyanophenyl group or 6-methyl-2-pyridine group).

Therefore, compounds shown in Table 3 can be mentioned as the compound of the present invention.

The invention [9] lies in a process for producing a Sym-triindole derivative represented by the general formula (11), which comprises reacting an oxyindole compound represented by the general formula (12) with a phosphorus oxyhalide to obtain a Sym-halo-triindole derivative represented by the general formula (13) (first step), reacting it with a formylating agent in the presence of butyllithium to obtain a Sym-formyltriindole derivative represented by the general formula (14) (second step), and reacting it with a methylene compound represented by the general formula (9) (third step).

Firstly, description is made on the first step of the present invention, that is, the reaction of oxyindole with phosphorus oxyhalide.

Firstly, explanation is made on the oxyindole compound represented by the general formula (12) used as a raw material.

TABLE 3

[Formula 37]

| Compound No. | Substitution position (each of three) | $R_8$ | $R_9$ | $R_{10}$ | Melting point (° C.) |
|---|---|---|---|---|---|
| 43 | 5 | CN | CN | n-Hex | 254-258 |
| 44 | 5 | CN | COOEt | n-Hex | 145-153 |
| 45 | 5 | CN | -C6H4-NO2 | n-Hex | 300 or higher |
| 46 | 5 | CN | 4-pyridyl | n-Hex | 255-260 |
| 47 | 5 | CN | CN | (2-Et)Hex | 290(decomposed) |
| 48 | 4 | CN | CN | n-Hex | |
| 49 | 6 | CN | CN | n-Hex | |
| 50 | 7 | CN | CN | n-Hex | |
| 51 | 5 | CN | N-methylpyridinium iodide | n-Hex | 236-238 |
| 52 | 5 | CN | -C6H4-NO2 | (2-Et)Hex | 267-272 |
| 53 | 5 | CN | COOH | (2-Et)Hex | 298-301 |

In the general formula (12), $R_{10}$ is, for example, a straight chain or branched chain C2-C12 alkyl group such as ethyl group, n-propyl group, n-butyl group, n-pentyl group, n-hexyl group, isopropyl group, 2-ethylhexyl group or the like; or a straight chain or branched chain C2-C12 haloalkyl group such as chloroethyl group, dichloroethyl group, trifluoroethyl group or the like.

Therefore, as the oxyindole compound represented by the general formula (12), usable in the present invention, there can be mentioned, for example, N-ethyl-4-bromooxyindole, N-ethyl-5-bromooxyindole, N-ethyl-6-bromooxyindole, N-ethyl-7-bromooxyindole, N-(n-propyl)-5-bromooxyindole, N-(n-butyl)-5-bromooxyindole, N-(n-pentyl)-5-bromooxyindole, N-(n-hexyl)-5-bromooxyindole, N-(isopropyl)-5-bromooxyindole, and N-(2-ethylhexyl)-5-bromooxyindole.

The oxyindole used in the present invention is known or can be produced by reacting a corresponding aniline with chloroacetyl chloride in the presence of aluminum chloride.

The molar ratio of the oxyindole used as a raw material and the phosphorus oxyhalide may be any molar ratio as long as stirring is possible. However, the preferred amount of the phosphorus oxyhalide is, for example, 0.5 to 30 liters, preferably 1 to 10 liters relative to 1 mole of the oxyindole.

As the phosphorus oxyhalide, there can be mentioned, for example, phosphorus oxychloride and phosphorus oxybromide. Ordinarily, phosphorus oxychloride is used preferably.

The temperature of the reaction may be any temperature as long as the reaction proceeds at the temperature, but is preferred to be, for example, 80° C. to the reflux temperature.

The period of the reaction is not particularly restricted but is preferred to be, for example, 1 to 48 hours.

Next, description is made on the formylation of the second step.

The second step of the present invention is a step for reacting the Sym-halo-indole represented by the general formula (13) with a formylating agent in the presence of butyllithium to produce a Sym-formyltriindole represented by the general formula (14).

As the formylating agent used in the present invention, there can be mentioned, for example, dimethylformamide, diethylformamide, formamide, N-formylpiperidine and N-formylpyrrolidine. Dimethylformamide and N-formylpiperidine are preferred. The molar ratio of the formylating agent and the Sym-halo-triindole derivative of the general formula (13) (a raw material) may be any molar ratio as long as the reaction is not impaired; however, the amount of the formylating agent is, for example, 3 to 30 moles, preferably 3 to 9 moles relative to 1 mole of the Sym-halo-triindole derivative represented by the general formula (13).

Butyllithium is simultaneously used in the present invention. The molar ratio of the butyllithium used in the present invention may be any molar ratio as long as the reaction is not impaired. However, the amount of the butyllithium is, for example, 3 to 15 moles, preferably 3 to 6 moles relative to 1 mole of the Sym-halo-triindole derivative represented by the general formula (13).

The present step is generally conducted using a solvent. As the solvent used in the present step, there can be mentioned, for example, aromatic hydrocarbons such as toluene, xylene and the like; chain or cyclic ethers such as diethyl ether, diisopropyl ether, tetrahydrofuran (THF), dioxane and the like; and hexamethylphosphoric triamide (HMPA). Tetrahydrofuran (THF) is preferred. The solvent used in the reaction may be a single solvent or a mixed solvent of any mixing ratio.

The amount of the solvent used in the reaction may be any amount as long as stirring is possible, but is preferred to be, for example, 0.1 to 10 liters relative to 1 mole of the Sym-halo-triindole derivative which is a raw material.

The temperature of the reaction may be any temperature as long as the reaction proceeds at the temperature, but is preferred to be, for example, −100° C. to the reflux temperature of the solvent used, preferably −78 to 30° C.

The period of the reaction is not particularly restricted but is, for example, 0.5 to 48 hours.

The third step is a step for reacting the Sym-formyltriindole derivative represented by the general formula (14), obtained in the second step, with a methylene compound represented by the general formula (9) to produce a Sym-triindole derivative represented by the general formula (11).

In the methylene compound represented by the general formula (9), used in the reaction of the third step, $R_8$ is hydrogen atom or cyano group; and $R_9$ is cyano group, carboxylic acid group (e.g. carboxylic acid, sodium carboxylate, potassium carboxylate, lithium carboxylate or pyridinium carboxylate), C1-C6 alkoxycarbonyl group (e.g. methoxycarbonyl group or ethoxycarbonyl group), aryloxycarbonyl group (e.g. phenoxycarbonyl group), aryl group [e.g. phenyl group, naphthyl group, or aromatic heterocyclic ring group of single ring or condensed ring containing nitrogen, oxygen or sulfur as heterocyclic atom, such as 2-pyridyl group, 3-pyridyl group, 4-pyridyl group, 2-pyrimidine group, 4-pyrimidine group, triazine group, pyrazolyl group, triazolyl group, quinolinyl group, indolyl group, isoindolyl group, thienyl group, benzothienyl group, furyl group, benzofuryl group, thiazolyl group, benzothiazolyl group, oxazolyl group, isoxazolyl group, benzoxazolyl group, thiadiazolyl group, benzothiadiazolyl group or the like], or substituted aryl group (e.g. 2-nitrophenyl group, 3-nitrophenyl group, 4-nitrophenyl group, 4-formylphenyl group, 4-cyanophenyl group or 6-methyl-2-pyridine group).

Therefore, as the methylene compound represented by the general formula (9), usable in the reaction of the third step, there can be mentioned, for example, acetonitrile, malononitrile, methyl acetate, ethyl acetate, cyanoacetic acid, methyl cyanoacetate, ethyl cyanoacetate, phenyl cyanoacetate, (4-nitrophenyl)cyanoacetate, 2-cyanomethylpyridine, 3-cyanomethylpyridine, 4-cyanomethylpyridine, 2-cyanomethylpyridine, benzyl cyanide and 4-nitrobenzyl cyanide. The molar ratio of the methylene compound represented by the general formula (9), used in the reaction may be any molar ratio as long as the reaction is not impaired. However, the amount of the methylene compound is 0.1 to 30 moles, preferably 1 to 10 moles relative to 1 mole of the Sym-formyltriindole derivative represented by the general formula (14).

The reaction is ordinarily conducted using a solvent. As the solvent used in the reaction, there can be mentioned, for example, aprotic polar solvents such as dimethylformamide, dimethylacetamide, diethylacetamide, N-methylpyrrolidone, N,N-dimethylimidazolinone, tetramethylurea and the like; aromatic hydrocarbons such as toluene, xylene, chlorobenzene and the like; chain or cyclic ethers such as diethyl ether, diisopropyl ether, tetrahydrofuran (THF), dioxane and the like; acetic acid esters such as methyl acetate, ethyl acetate, butyl acetate and the like; and nitrites such as acetonitrile and the like. The solvent used in the reaction may a single solvent or a mixed solvent of any mixing ratio.

The amount of the solvent used in the reaction may be any as long as stirring is possible. However, the preferred amount is, for example, 0.1 to 30 liters, preferably 0.5 to 10 liters relative to 1 mole of the Sym-formyltriindole derivative of the general formula (14) which is a raw material.

The temperature of the reaction may be any temperature as long as the reaction proceeds at the temperature, but is preferred to be, for example, −20° C. to the reflux temperature of the solvent used.

The period of the reaction is not particularly restricted but is preferred to be, for example, 1 to 48 hours.

The invention [10] is described. This invention is the third step of the invention [9].

The invention [11] is described. This invention is the second step of the invention [9].

The invention [12] is described. This invention lies in a Sym-triindole derivative represented by the general formula (15). In the general formula (15), $R_{10}$ has the same definition as given above; and $R_{11}$ is, for example, aryl group (e.g. phenyl group, 2-pyridyl group, 3-pyridyl group, 4-pyridyl group or 2-pyrimidine group), or substituted aryl group [e.g. 4-nitrophenyl group, 4-cyanophenyl group, or 4-(methoxycarbonyl)phenyl group].

Therefore, for example, compounds shown in Table 4 can be mentioned as the compound of the present invention.

TABLE 4

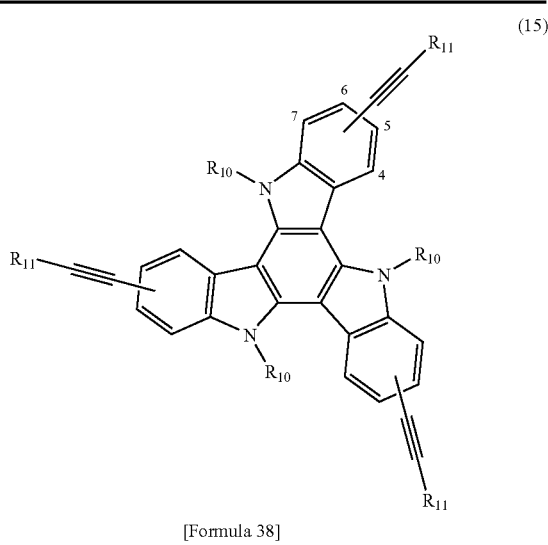

[Formula 38]

| Compound No. | Substitution position (each of three) | $R_{10}$ | $R_{11}$ | Melting point (° C.) |
|---|---|---|---|---|
| 54 | 5 | n-Hex | Ph | 180-189 |
| 55 | 4 | n-Hex | Ph | |
| 56 | 6 | n-Hex | Ph | |
| 57 | 7 | n-Hex | Ph | |
| 58 | 5 | (2-Et)Hex | Ph | |
| 59 | 5 | n-Hex | 4-Py | |
| 60 | 5 | (2-Et)Hex | 4-Py | |

The invention [13] is described.

The present invention lies in a process for producing a Sym-triindole derivative represented by the general formula (15), which comprises reacting a Sym-halo-triindole derivative represented by the general formula (13), with an acetylene derivative represented by the general formula (16).

In the general formula (16), $R_{11}$ is, for example, aryl group (e.g. phenyl group, 2-pyridyl group, 3-pyridyl group, 4-pyridyl group or 2-pyrimidine group), or substituted aryl group [e.g. 4-nitrophenyl group, 4-cyanophenyl group or 4-(methoxycarbonyl)phenyl group]; and $R_{12}$ is hydrogen atom or trimethylsilyl group.

Therefore, as the acetylene derivative of the general formula (16) used in the reaction, there can be mentioned, for example, phenylacetylene, 1-phenyl-2-trimethylsilylacetylene, (pyridin-2-yl)acetylene, (pyridin-3-yl)acetylene, (pyridin-4-yl)acetylene, (4-cyanophenyl)acetylene, and 1-(pyridin-4-yl)-2-trimethylsilylacetylene.

In the reaction, the molar ratio of the Sym-halo-triindole derivative represented by the general formula (13) and the acetylene derivative represented by the general formula (16) may be any molar ratio. However, the amount of the acetylene derivative represented by the general formula (16) is preferably 3 to 10 moles per 1 mole of the Sym-halo-triindole derivative represented by the general formula (13).

The reaction is conducted generally using a solvent. As the solvent usable in the reaction, there can be mentioned, for example, aromatic hydrocarbons such as toluene, xylene, chlorobenzene and the like; halogenated aliphatic hydrocarbons such as dichloromethane, chloroform and the like; aprotic polar solvents such as dimethylformamide, diethylformamide, N-methylpyrrolidone, dimethylacetamide and the like; chain or cyclic ethers such as diethyl ether, tetrahydrofuran (THF), dioxane and the like; alcohols such as methanol, ethanol and the like; polyethylene glycols such as PEG-400 and the like; nitrites such as acetonitrile and the like; nitrogen-containing bases such as pyrrolidine, triethylamine, pyridine and the like; and water. The solvent used in the present reaction may be a single solvent or a mixed solvent of any mixing ratio.

The amount of the solvent used in the reaction may be any amount as long as stirring is possible; however, the amount is preferably 0.1 to 20 liters relative to 1 mole of the Sym-halo-triindole derivative of the general formula (13) which is a raw material.

The temperature of the reaction may be any temperature as long as the reaction proceeds at the temperature, but is preferred to be, for example, 20° C. to the reflux temperature of the solvent used.

The period of the reaction is not particularly restricted but is preferred to be, for example, 1 to 48 hours.

The invention [1,4] is described. This invention is the first step of the invention [9]

EXAMPLES

Next, the processes for producing the present invention compounds are specifically described by way of Examples. However, the present invention is in no way restricted by these Examples.

Example 1

Production of Sym-N-(n-hexyl)-5-bromotriindole

In a 500-ml, three-necked flask provided with a magnetic stirrer, a reflux condenser and a thermometer were placed 40 g of N-(n-hexyl)-5-bromooxyindole and 240 ml of phosphorus oxychloride. Refluxing was conducted with heating, for 8 hours, to give rise to a reaction. After the completion of the reaction, phosphorus oxychloride was recovered under reduced pressure. To the resulting reside were added water and a sodium hydroxide aqueous solution under cooling. The resulting crystals were collected by filtration and dissolved in 300 ml of toluene. The resulting solution was hot-filtered to remove the insolubles. The filtrate (toluene layer) washed with water and then concentrated. The concentrate (residue) was recrystallized (toluene:ethyl acetate=1:9) to obtain 10.9 g of Sym-N-(n-hexyl)-5-bromotriindole. Yield: 29%

Melting point: 205-207° C. FAB-Mass (NBA, Positive): [(M+H)$^+$]=835 $^1$H-NMR (300 MHz, CDCl$_3$), δ (ppm): 0.84 (t, J=6.6 Hz, 9H), 1.20-1.41 (m, 18H), 1.88-2.20 (br, 6H), 4.59 (t, J=8.1 Hz, 6H), 7.41 (t, J=8.7 Hz, 3H), 7.52 (dd, J=1.5, 8.7 Hz, 3H), 8.21 (d, J=1.5 Hz, 3H)

Example 2

Production of Sym-N-(n-hexyl)-5-phenyltriindole

In a 50-ml, three-necked flask provided with a magnetic stirrer, a reflux condenser and a thermometer were placed, in an argon atmosphere, 165 mg of Sym-N-(n-hexyl)-5-bromotriindole, 35 mg of tetrakistriphenylphosphine palladium (O) and 20 ml of toluene. Thereto were added a solution of 109 mg of phenylboronic acid in 5 ml of ethanol and 10 ml of a saturated sodium bicarbonate aqueous solution. Refluxing was conducted with heating, for 5 hours, to give rise to a reaction. Aster the completion of the reaction, the system was cooled to room temperature and filtered. To the resulting filtrate were added 50 ml of ethyl acetate and 30 ml of a saturated sodium chloride aqueous solution, for layer separation. The resulting ethyl acetate layer was concentrated. The concentrate was subjected to silica gel column chromatography (chloroform) to obtain 39 mg of Sym-N-(n-hexyl)-5-phenyltriindole. Yield: 23.8%

FAB-Mass (NBA, positive): [(M+H)$^+$]=826 $^1$H-NMR (270 MHz, CDCl$_3$), δ (ppm): 0.74 (t, J=7.1 Hz, 9H), 1.10-1.25 (m, 18H), 2.00-2.10 (br, 6H), 4.96 (t, J=7.9 Hz, 6H), 7.30-7.41 (m, 3H), 7.48-7.55 (m, 6H), 7.64-7.78 (m, 12H), 8.49 (s, 3H)

Example 3

Production of Sym-N-(n-hexyl)-5-(4-formylphenyl)triindole

In Example 2, phenylboronic acid was replaced by 150 mg of 4-formylphenylboronic acid, whereby was obtained 35 mg of Sym-N-(n-hexyl)-5-(4-formylphenyl)triindole. Yield: 19.3%

Melting point: 245-257° C. FAB-Mass (NBA, Positive): [(M+H)$^+$]=910 $^1$H-NMR (270 MHz, CDCl$_3$), δ (ppm): 0.73 (t, J=7.1 Hz, 9H), 1.00-1.30 (m, 18H), 2.00-2.20 (br, 6H), 4.98 (t, J=8.1 Hz, 6H), 7.74 (s, 6H), 7.91 (d, J=8.2 Hz, 6H), 8.03 (d, J=8.6 Hz), 8.54 (s, 3H), 10.10 (s, 3H)

Example 4

Production of Sym-N-(n-hexyl)-5-(4-ethoxycarbonylphenyl)triindole

In Example 2, phenylboronic acid was replaced by 247 mg of ethyl 4-(4,4,5,5-tetramethyl-1,3,2-dioxaborolane-2-yl) benzoate, whereby was obtained by 78 mg of Sym-N-(n-hexyl)-5-(4-ethoxycarbonylphenyl)triindole. Yield: 37.7%

Melting point: 203-213° C. FAB-Mass (NBA, Positive): [(M+H)$^+$]=1042 $^1$H-NMR (270 MHz, CDCl$_3$), δ (ppm): 0.74 (t, J=7.1 Hz, 6H), 1.02-1.28 (m, 18H), 1.45 (t, J=6.9, 7.2 Hz, 9H), 2.00-2.18 (br, 6H), 4.44 (q, J=6.9, 7.2 Hz, 6H), 4.92 (t, J=7.9 Hz, 6H), 7.68-7.74 (m, 6H), 7.80 (d, J=8.2 Hz, 6H), 8.19 (d, J=8.2 Hz, 6H), 8.50 (s, 3H)

Example 5

Production of Sym-N-(n-hexyl)-5-(4-cyanophenyl)triindole

In Example 2, phenylboronic acid was replaced by 206 mg of 4-(4,4,5,5-tetramethyl-1,3,2-dioxaborolane-2-yl)benzonitrile, whereby was obtained 21.5 mg of Sym-N-(n-hexyl)-5-(4-cyanophenyl)triindole. Yield: 11.9%

Melting point: 297-303° C. FAB-Mass (NBA, Positive): [(M+H)$^+$]=901 $^1$H-NMR (270 MHz, CDCl$_3$), δ (ppm): 0.74 (t, J=7.1 Hz, 9H), 1.05-1.25 (m, 18H), 1.98-2.11 (br, 6H), 4.94 (t, J=7.5 Hz, 6H), 7.69 (d, J=8.1 Hz, 3H), 7.73 (d, J=8.4 Hz, 3H), 7.79 (d, J=8.7 Hz, 6H), 7.83 (d, J=8.6 Hz, 6H), 8.46 (s, 3H)

Example 6

Production of Sym-N-(n-hexyl)-5-(4-(2,2-dicyanovinyl)phenyl)triindole

In a 50-ml, three-necked flask provided with a magnetic stirrer, a reflux condenser and a thermometer were placed, in an argon atmosphere, 50 mg of Sym-N-(n-hexyl)-5-(4-formylphenyl)triindole, 16 mg of malononitrile and 5.5 ml of THF. Thereto were added 0.165 mg of acetic acid and 2.3 mg of pyrrolidine. Stirring was conducted at room temperature for 4 hours to give rise to a reaction. After the completion of the reaction, the reaction mixture was concentrated. The concentrate (residue) was subjected to silica gel column chromatography (chloroform) to obtain 25 mg of Sym-N-(n-hexyl)-5-(4-(2,2-dicyanovinyl)phenyl)triindole. Yield: 43.2%

Melting point: 281-291° C. FAB-Mass (NBA, Positive): [(M+H)$^+$]=1054

Example 7

Production of Sym-N-(n-hexyl)-5-methyltriindole

In a 100-ml, three-necked flask provided with a magnetic stirrer, a reflux condenser and a thermometer were placed 7.60 g of N-(n-hexyl)-5-methyloxyindole and 60 ml of phosphorus oxychloride. They were subjected to a reaction at 100° C. for 11 hours. After the completion of the reaction, phosphorus oxychloride was recovered. Water was added and neutralization was made with sodium hydroxide. The resulting crystals were collected by filtration and dissolved in 250 ml of toluene. The toluene solution was filtered to remove the insolubles. The filtrate washed with water, dried with sodium sulfate, and concentrated, after which recrystallization (toluene:ethyl acetate=1:9) was conducted to obtain 2.16 g of Sym-N-(n-hexyl)-5-methyltrindole. Yield: 31%

Melting point: 160° C. EI-Mass: (M$^+$)=639 $^1$H-NMR (300 MHz, CDCl$_3$), δ (ppm): 0.83 (t, J=6.6 Hz, 9H), 1.20-1.45 (m, 18H), 2.03 (quint, J=7.8 Hz, 6H), 2.61 (s, 9H), 4.83 (t, J=8.1 Hz, 6H), 7.25 (bd, J=8.4 Hz, 3H), 7.50 (d, J=8.4 Hz, 3H), 8.06 (bs, 3H)

Example 8

Production of Sym-N-(n-hexyl)-5-formyltriindole

In a 300-ml, three-necked flask provided with a magnetic stirrer, a reflux condenser and a thermometer were placed, in a nitrogen atmosphere, 1.5 g of Sym-N-(n-hexyl)-5-bromotriindole and 180 ml of tetrahydrofuran (THF). They were cooled to −78° C. Thereto was dropwise added 6.9 ml of 1.57 M n-butyllithium slowly and a reaction was allowed to take place for 1 hour at the same temperature. Then, 1.2 g of N-formylpiperidine was added slowly and a reaction was allowed to take place at −78° C. for 1 hour. The reaction mixture was heated to 0° C. and diluted hydrochloric acid was added for hydrolysis. Then, extraction with toluene was conducted. The toluene layer was dried with sodium sulfate and concentrated. The concentrate (residue) was recrystallized (tetrahydrofuran, THF) to obtain 1.01 g of Sym-N-(n-hexyl)-5-formyltriindole. Yield: 82%

Melting point: 185-187° C. FAB-Mass (NBA, Positive): (M$^+$)=681 IR (KBr, cm$^{-1}$): 1687 $^1$H-NMR (300 MHz, CDCl$_3$), δ (ppm): 0.80 (t, J=7.2 Hz, 9H), 1.20-1.40 (m, 18H), 2.03 (br, 6H), 4.93 (t, J=7.8 Hz, 6H), 7.72 (d, J=8.7 Hz, 3H), 8.02 (dd, J=0.9, 8.4 Hz, 3H), 8.77 (d, J=1.2 Hz, 3H), 10.17 (s, 3H) Elemental Analysis: Calculated for C$_{45}$H$_{51}$N$_3$O$_3$ (%): C, 79.26; H, 7.54; N, 6.16.

Measured: C, 79.20; H, 7.49; N, 6.19.

Example 9

Production of Sym-N-(n-hexyl)-5-(2,2-dicyanovinyl)triindole

In a 50-ml, three-necked flask provided with a magnetic stirrer, a reflux condenser and a thermometer were placed 1.00 g of Sym-N-(n-hexyl)-5-formyltriindole, 0.437 g of malononitrile, 62.4 mg of piperidine, 4.40 mg of acetic acid and 10 ml of tetrahydrofuran (THF). A reaction was conducted at 50° C. for 3 hours. After the completion of the reaction, the solvent was removed by distillation. The resulting residue was recrystallized using tetrahydrofuran (THF) to obtain 0.681 g of Sym-N-(n-hexyl)-5-(2,2-dicyanovinyl)triindole. Yield: 56%

Melting point: 254-258° C. FAB-Mass (NBA, Positive): [(M+H)$^+$]=826 IR (KBr, cm$^{-1}$): 2223 $^1$H-NMR (300 MHz, CDCl$_3$), δ (ppm): 0.69 (t, J=7.2 Hz, 9H), 1.05-1.30 (m, 18H), 1.82 (br, 6H), 5.09 (t, J=7.2 Hz, 6H), 7.79 (d, J=8.7 Hz, 3H), 7.94 (s, 3H), 7.97 (dd, J=1.0, 8.7 Hz, 3H), 8.95 (d, J=1.0 Hz, 3H) Elemental Analysis: Calculated for C$_{54}$H$_{51}$N$_9$ (%): C, 78.52; H, 6.22; N, 15.26. Measured: C, 78.30; H, 6.26; N, 15.16.

Example 10

Production of Sym-N-(n-hexyl)-(2-cyano-2-ethoxycarbonylvinyl)triindole

In a 50-ml, three-necked flask provided with a magnetic stirrer, a reflux condenser and a thermometer were placed 100 mg of Sym-N-(n-hexyl)-5-formyltriindole, 74.8 mg of ethyl cyanoacetate, 6.3 mg of piperidine and 15 m of tetrahydrofuran (THF). A reaction was conducted at 50° C. for 12 hours. After the completion of the reaction, the solvent was removed by distillation. The residue was recrystallized using tetrahydrofuran (THF) to obtain 99.5 mg of Sym-N-(n-hexyl)-(2-cyano-2-ethoxycarbonylvinyl)triindole. Yield: 70%

Melting point: 145-153° C. FAB-Mass (NBA, Positive): [(M+H)$^+$]=967 IR (KBr, cm$^{-1}$): 1590 $^1$H-NMR (300 MHz, CDCl$_3$), δ (ppm): 0.68 (t, J=7.2 Hz, 9H), 1.05-1.18 (m, 18H), 1.45 (t, J=7.2 Hz, 9H), 1.78-1.91 (bs, 6H), 4.44 (q, J=7.2 Hz, 6H), 5.10 (t, J=8.1 Hz, 6H), 7.76 (d, J=8.7 Hz, 3H), 8.13 (dd, J=1.0, 8.7 Hz, 3H), 8.49 (s, 3H), 8.99 (d, J=1.0 Hz, 3H)

Example 11

Production of Sym-N-(n-hexyl)-[2-cyano-2-(4-nitrophenyl)vinyl]triindole

In a 50-ml, three-necked flask provided with a magnetic stirrer, a reflux condenser and a thermometer were placed 100 mg of Sym-N-(n-hexyl)-5-formyltriindole, 107 mg of 4-nitrobenzyl cyanide, 6.3 mg of piperidine and 15 ml of tetrahydrofuran (THF). A reaction was conducted at 50° C. for 12 hours. After the completion of the reaction, the resulting crystals were collected by filtration to obtain 117 mg of Sym-N-(n-hexyl)-[2-cyano-2-(4-nitrophenyl)vinyl]triindole.

Melting point: 300° C. or higher FAB-Mass (NBA, Positive): [(M+H)$^+$]=1114 IR (KBr, cm$^{-1}$): 2212, 1340

Example 12

Production of Sym-N-(n-hexyl)-[2-cyano-2-(4-pyridyl)vinyl]triindole

In a 50-ml, three-necked flask provided with a magnetic stirrer, a reflux condenser and a thermometer were placed 100 mg of Sym-N-(n-hexyl)-5-formyltriindole, 120 mg of 4-cyanomethylpyridine, 6.3 mg of piperidine and 15 ml of tetrahydrofuran (THF). A reaction was conducted at 50° C. for 4 hours. After the completion of the reaction, the reaction mixture was subjected to silica gel column chromatography to obtain 131 mg of Sym-N-(n-hexyl)-[2-cyano-2-(4-pyridyl)vinyl]triindole. Yield: 91%

Melting point: 255-260° C. FAB-Mass (NBA, Positive): [(M+H)$^+$]=983 IR (KBr, cm$^{-1}$): 2210 $^1$H-NMR (300 MHz, CDCl$_3$), δ (ppm): 0.64 (t, J=7.2 Hz, 9H), 0.90-1.14 (m, 18H), 1.82 (br, 6H), 4.81 (t, J=7.2 Hz, 6H), 7.52 (d, J=8.7 Hz, 3H), 7.59-7.61 (m, 6H), 7.82 (s, 3H), 7.96 (dd, J=1.0, 8.7 Hz, 3H), 8.63 (bs, 3H), 8.71-8.73 (m, 6H)

Example 13

Production of Sym-N-(2-ethylhexyl)-5-bromotriindole

In a 100-ml, three-necked flask provided with a magnetic stirrer, a reflux condenser and a thermometer were placed 5.0 g of N-(2-ethylhexyl)-5-bromooxyindole and 30 ml of phosphorus oxychloride. A reaction was conducted at 100° C. for 11 hours. After the completion of the reaction, phosphorus oxychloride was recovered under reduced pressure. To the residue were added water and sodium hydroxide for neutralization. Then, extraction with toluene was conducted. The toluene layer was concentrated and the concentrate was subjected to silica gel column chromatography to obtain 1.11 g of Sym-N-(2-ethylhexyl)-5-bromotriindole. Yield: 24%

EI-MS (M$^+$): 918 Melting point: 161° C. $^1$H-NMR (300 MHz, CDCl$_3$), δ (ppm): 0.26-0.33 (m, 9H), 0.56-0.65 (m, 9H), 0.74-1.04 (m, 24H), 1.61-1.72 (br, 3H), 4.07 (d, J=7.2 Hz, 6H), 7.42 (d, J=8.7 Hz, 3H), 7.58 (dd, J=1.5, 8.7 Hz, 3H), 7.75 (bs, 3H)

Example 14

Production of Sym-N-(2-ethylhexyl)-5-formyltriindole

In a 100-ml, three-necked flask provided with a magnetic stirrer, a reflux condenser and a thermometer were placed, in a nitrogen stream, 1.1 g of Sym-N-(2-ethylhexyl)-5-bromotriindole and 50 ml of tetrahydrofuran (THF). They were cooled to −78° C. Thereto were dropwise added 4.2 ml of 1.57 M n-butyllithium slowly, followed by aging at the same temperature for 1 hour. Then, 0.74 g of N-formylpiperidine was added dropwise slowly. A reaction was conducted at −78° C. for 1 hour. Thereafter, the system was heated to 0° C.; diluted hydrochloric acid was added for hydrolysis; and extraction with toluene was conducted. The toluene layer was concentrated and the concentrate was subjected to silica gel column chromatography to obtain 0.80 g of Sym-N-(2-ethylhexyl)-5-formyltriindole. Yield: 87%

Melting point: 243° C. FAB-Mass (NBA, Positive): (M$^+$)= 765 IR (KBr, cm$^{-1}$): 1684 $^1$H-NMR (300 MHz, CDCl$_3$), δ (ppm): 0.33-0.39 (m, 9H), 0.52-0.60 (m, 9H), 0.61-0.96 (m, 24H), 1.74-1.88 (br, 3H), 4.67 (d, J=6.3 Hz, 6H), 7.62 (d, J=8.4 Hz, 3H), 8.06 (dd, J=1.2, 8.4 Hz, 3H), 8.51 (bs, 3H), 10.26 (s, 3H)

Example 15

Production of Sym-N-(2-ethylhexyl)-5-(2,2-dicyanovinyl)triindole

In a 500-ml, three-necked flask provided with a magnetic stirrer, a reflux condenser and a thermometer were placed 0.80 g of Sym-N-(2-ethylhexyl)-5-formyltriindole, 0.31 g of malononitrile, 62.4 mg piperidine and 150 ml of tetrahydrofuran (THF). A reaction was conducted at 50° C. for 3 hours. After the completion of the reaction, the reaction mixture was concentrated. The residue was recrystallized using tetrahydrofuran (THF) to obtain 0.15 g of Sym-N-(2-ethylhexyl)-5-(2,2-dicyanovinyl)triindole. Yield: 16%

Melting point: 290° C. (decomposed) FAB-Mass (NBA, Positive): [(M+H)$^+$]=910 IR (KBr, cm$^{-1}$): 2224 $^1$H-NMR (300 MHz, CDCl$_3$), δ (ppm): 0.43-0.56 (m, 9H), 0.62-0.70 (m, 9H), 0.72-1.11 (m, 24H), 1.86-2.20 (br, 3H), 4.99-5.60 (m, 6H), 7.76 (d, J=8.4 Hz, 3H), 7.93 (s, 3H), 9.11 (bs, 3H)

Example 16

Production of Sym-N-(n-hexyl)-5-(phenylethynyl)triindole

In a 100-ml, three-necked flask provided with a magnetic stirrer, a reflux condenser and a thermometer were placed, in a nitrogen stream, 100 mg of Sym-N-(n-hexyl)-5-bromotriindole, 8.35 mg of bistriphenylphosphine palladium dichloride, 2.27 mg of copper (I) iodide, 4 ml of triethylamine and 4 ml of toluene. A reaction was conducted at 70° C. for 9 hours. After the completion of the reaction, the reaction mixture was cooled to room temperature and neutralized with diluted hydrochloric acid. Extraction with toluene was conducted. The organic layer washed with water and a saturated sodium chloride aqueous solution. The toluene layer was concentrated and the concentrate was subjected to silica gel column chromatography to obtain 10 mg of Sym-N-(n-hexyl)-5-(phenylethynyl)triindole. Yield: 9.3%

Melting point: 180-189° C. IR (KBr, cm$^{-1}$): 2927, 1565, 1494 $^1$H-NMR (300 MHz, CDCl$_3$), δ (ppm): 0.758 (t, J=7.2 Hz, 9H), 1.15-1.50 (m, 18H), 2.00-2.17 (m, 6H), 4.79-4.87 (m, 6H), 7.34-7.42 (m, 9H), 7.56-7.66 (m, 12H), 8.418 (s, 3H)

Example 17

Production of methyl iodide salt of Sym-N-(n-hexyl)-5-[2-cyano-2-(4-pyridyl)vinyl]triindole In a 25-ml reaction flask provided with a magnetic stirrer, a reflux condenser and a thermometer were placed 100 mg (0.10 mmol) of Sym-N-(n-hexyl)-5-[2-cyano-2-(4-pyridyl) vinyl]triindole and 2 ml of methyl iodide. Stirring was conducted at room temperature for 12 hours. The reaction mixture was concentrated under reduced pressure. The residue washed with hexane, toluene, ethyl acetate and tetrahydrofuran. The resulting crude crystals were dissolved in a small amount of methanol. Thereto was added dichloromethane to give rise to recrystallization, to obtain 114 mg of dark brown crystals. Yield: 81%

Melting point: 236-238° C. IR (KBr, cm$^{-1}$): 2214 $^1$H-NMR (300 MHz, DMSO-d$_6$), δ (ppm): 0.44 (t, J=6.9 Hz, 9H), 0.72-0.98 (m, 24H), 1.71 (m, 6H), 4.34 (s, 9H), 5.22 (m, 6H), 8.27 (d, J=9.3 Hz), 8.39 (d, J=9.0 Hz, 3H), 8.44 (d, J=6.6 Hz), 9.01 (s, 3H), 9.04 (d, J=6.9 Hz, 6H), 9.11 (s, 3H)

Example 18

Production of Sym-N-(2-ethylhexyl)-5-[2-cyano-2-(4-nitrophenyl)vinyl]triindole

In a 25-ml reaction flask provided with a magnetic stirrer, a reflux condenser and a thermometer were placed 200 mg (0.26 mmol) of Sym-N-(2-ethylhexyl)-5-formyltriindole, 254 mg (1.56 mmol) of 4-cyanomethylnitrobenzene, 0.5 ml of piperidine and 5 ml of tetrahydrofuran. Stirring was conducted at 65° C. for 12 hours. After confirmation of the disappearance of the raw materials by TLC, water was added. The resulting reddish brown crystals were collected by filtration and washed with toluene. The resulting cake was purified by silica gel column chromatography to obtain 20 mg of orange crystals. Yield: 6%

Melting point: 267-272° C. IR (KBr, cm$^{-1}$): 854, 1340, 2210 $^1$H-NMR (300 MHz, CDCl$_3$), δ (ppm): 0.45-0.54 (m, 9H), 0.60-0.66 (m, 9H), 0.68-1.12 (m, 24H), 1.99 (m, 3H), 5.11 (m, 6H), 7.74 (d, J=8.4 Hz), 7.87-7.96 (m, 12H), 8.35 (d, J=8.7 Hz, 6H), 9.17 (s, 3H) Elemental Analysis: Calculated for C$_{75}$H$_{75}$N$_9$O$_6$ (%): C, 75.16; H, 6.31; N, 10.52. Measured: C, 75.13; H, 6.31; N, 10.38.

Example 19

Production of Sym-N-(2-ethylhexyl)-5-[2-cyano-2-hydroxycarbonylvinyl]triindole

In a 50-ml reaction flask provided with a magnetic stirrer, a reflux condenser and a thermometer were placed 371 mg (0.48 mmol) of Sym-N-(2-ethylhexyl)-5-formyltriindole, 618 mg (7.2 mmol) of cyanoacetic acid, 112 mg (1.44 mmol) of ammonium acetate and 20 ml of tetrahydrofuran (THF). Stirring was conducted at 65° C. for 12 hours. Toluene was added. The resulting yellow cake was collected by filtration and washed with water and toluene. The crude cake was dissolved in tetrahydrofuran. Toluene was added to give rise to recrystallization, and a cake was collected by filtration. The cake was subjected to silica gel column chromatography for purification. Recrystallization from tetrahydrofuran was conducted to obtain 376 mg of yellow crystals.

FAB-Mass (NBA, Positive): (M$^+$)=967 Melting point: 298-301° C. IR (KBr, cm$^{-1}$): 1716, 2224, 2960 $^1$H-NMR (300 MHz, DMSO-d$_6$), δ (ppm): 0.32-0.39 (m, 9H), 0.51 (m, 9H), 0.60-0.97 (m, 24H), 1.77 (m, 3H), 4.99 (m, 6H), 8.07 (d, J=8.7 Hz, 3H), 8.62 (s, 3H), 8.96 (s, 3H), 13.7 (bs, 3H) Elemental Analysis: Calculated for C$_{60}$H$_{66}$N$_6$O$_6$ (%): C, 74.51; H, 6.88; N, 8.69. Measured: C, 74.90; H, 6.93; N, 8.27.

Example 20

Production of Sym-N-(2-ethylhexyl)-5-cyanotriindole

In a 200-ml reaction flask provided with a magnetic stirrer, a reflux condenser and a thermometer were placed 150 mg (0.20 mmol) of Sym-N-(2-ethylhexyl)-5-formyltriindole, 50 mg of hydroxylamine hydrochloride, 60 mg of sodium acetate, 50 ml of methanol and 50 ml of toluene. Stirring was conducted at room temperature for 12 hours to give rise to a reaction. After the completion of the reaction, the solvent was removed by distillation under reduced pressure. The resulting crystals were washed with water and dried.

The above-obtained crystals, 100 ml of toluene and 1 g of acetic anhydride were placed in a 200-ml reaction flask provided with a magnetic stirrer, a reflux condenser and a thermometer, and refluxing with heating was conducted for 4 hours to give rise to a reaction. After the completion of the reaction, the reaction mixture was cooled to room temperature. 100 ml of water was added for layer separation. The toluene layer was concentrated. The residue obtained was subjected to column chromatography to obtain 14 mg of Sym-N-(2-ethylhexyl)-5-cyanotriindole. Yield: 9.2%

FAB-Mass (NBA, Positive): [(M+H)$^+$]=757 Melting point: 248° C. IR (KBr, cm$^{-1}$): 2219 $^1$H-NMR (270 MHz, CDCl$_3$), δ (ppm): 0.30-0.40 (m, 9H), 0.42-1.05 (m, 33H), 1.60-1.80 (m, 3H), 4.35 (d, J=7.2 Hz, 6H), 7.75 (d, J=8.2 Hz, 3H), 7.89 (dd, J=1 Hz, 8.9 Hz, 3H), 7.93 (s, 3H)

INDUSTRIAL APPLICABILITY

The present invention provides a novel substituted Sym-triindole derivative and a process for production thereof. The substituted Sym-triindole derivative is applicable to a wide spectrum of uses, such as various electrification preventions, electrification controls, capacitors, batteries, chemical sensors, displays, organic EL materials, solar cells, photodiodes, phototransistors, nonlinear materials, photorefractive materials, rustproof agents, adhesives, fibers, antistatic paints, electrodeposition paints, plating primers, electric corrosion protections and the like.

The invention claimed is:

1. A Sym-triindole derivative represented by the following general formula (3):

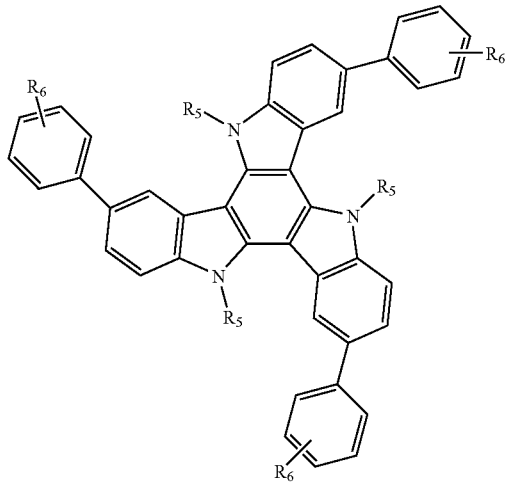

(3)

wherein $R_5$ is C2-C12 alkyl group, substituted C2-C12 alkyl group, C2-C12 haloalkyl group, or aryl C1-C6 alkyl group; and $R_6$ is hydrogen, formyl group, cyano group, C1-C6 alkoxycarbonyl group, dicyanovinyl group, aryl group or substituted aryl group.

2. A process for producing a Sym-triindole derivative represented by the following general formula (7):

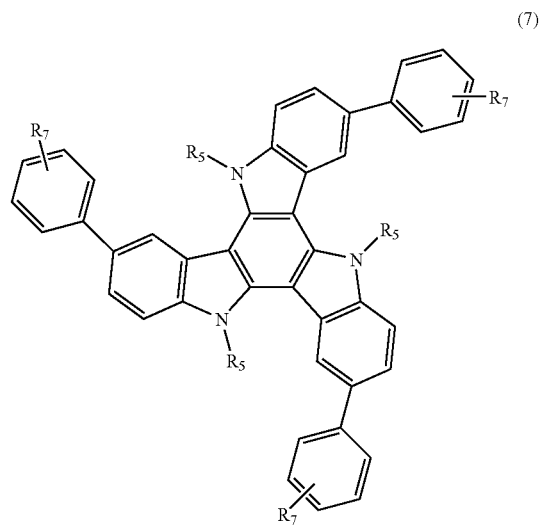

(7)

wherein $R_5$ is C2-C12 alkyl group, substituted C2-C12 alkyl group, C2-C12 haloalkyl group or aryl C1-C6 alkyl group; and $R_7$ is hydrogen, formyl group, cyano group, C1-C6 alkoxycarbonyl group, aryl group or substituted aryl group, which process comprises reacting an N-substituted5-halooxyindole represented by the following general formula (4):

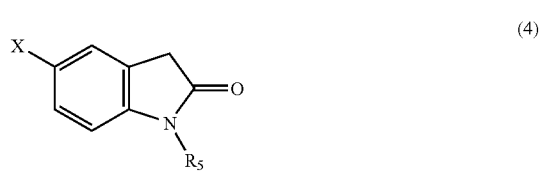

(4)

wherein $R_5$ has the same definition as given above; and X is halogen, with a phosphorus oxyhalide to obtain an N-substituted-5-halotriindole derivative represented by the following general formula (5):

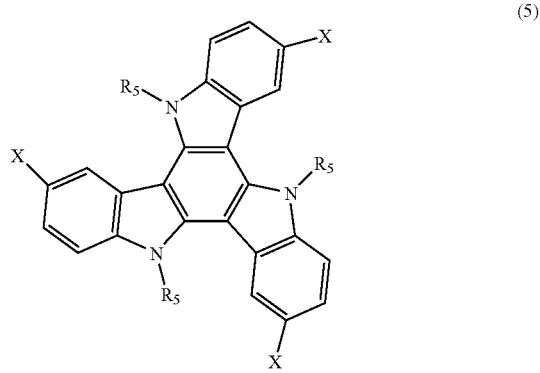

(5)

wherein $R_5$ and X have the same definitions as given above, and reacting the derivative of general formula (5) it with a boric acid compound represented by the following general formula (6):

(6)

wherein $R_7$ has the same definition as give above; and $R_a$ and $R_b$ are each independently hydrogen atom, C1-C6 alkyl group or optionally substituted phenyl group and may be combined to each other to form a ring.

3. A process for producing a Sym-triindole derivative represented by the following general formula (7):

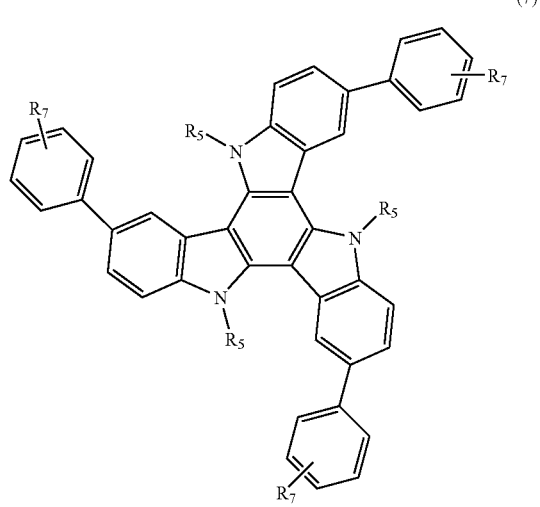

(7)

wherein $R_5$ is C2-C12 alkyl group, substituted C2-C12 alkyl group, C2-C12 haloalkyl group or aryl C1-C6 alkyl group; and $R_7$ is hydrogen, formyl group, cyano group, C1-C6 alkoxycarbonyl group, aryl group or substituted aryl group, which process comprises reacting an N-substituted-5-halo-triindole derivative represented by the following general formula (5):

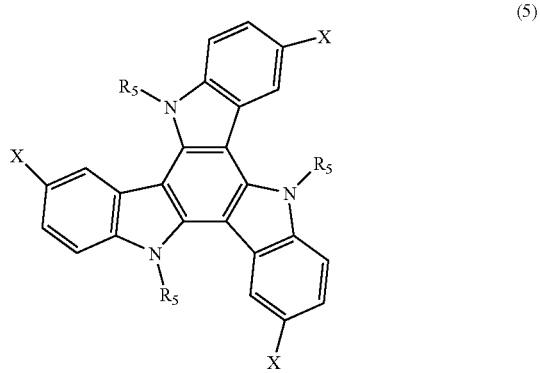

(5)

wherein $R_5$ has the same definition as given above; and X is halogen, with a boric acid compound represented by the following general formula (6):

(6)

wherein $R_7$ has the same definition as given above; and $R_a$ and $R_b$ are each independently hydrogen atom, C1-C6 alkyl group or optionally substituted phenyl group and may be combined to each other to form a ring.

4. A process for producing an N-substituted-5-halo-triindole derivative represented by the following general formula (5):

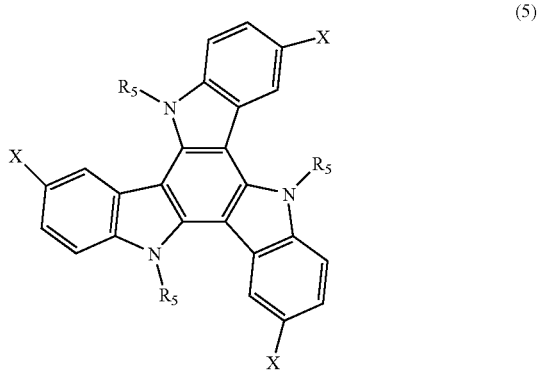

(5)

wherein $R_5$ is C2-C12 alkyl group, substituted C2-C12 alkyl group, C2-C12 haloalkyl group or aryl C1-C6 alkyl group; and X is halogen, which process comprises reacting an N-substituted-5-halo-oxyindole represented by the following general formula (4):

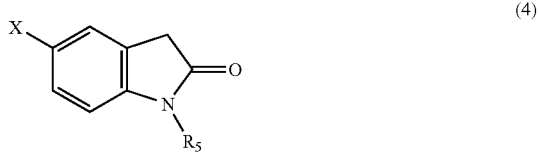

(4)

wherein $R_5$ and X have the same definitions as given above, with a phosphorus oxyhalide.

5. A process for producing a Sym-triindole derivative represented by the following general formula (10):

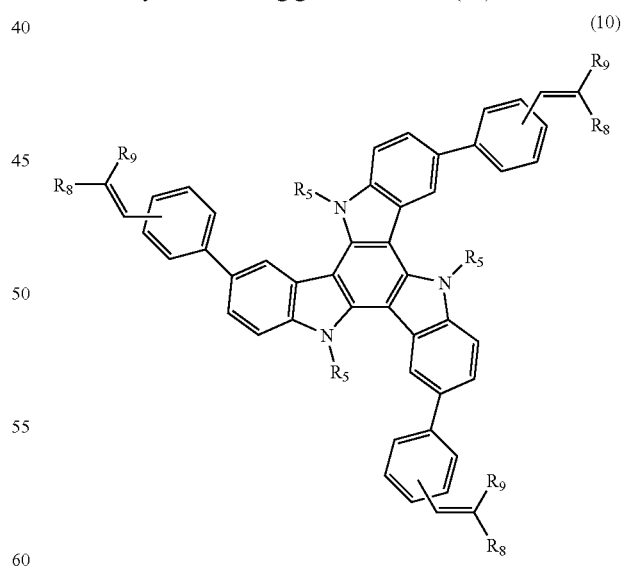

(10)

wherein $R_5$ is C2-C12 alkyl group, substituted C2-C12 alkyl group, C2-C12 haloalkyl group or aryl C1-C6 alkyl group; $R_8$ is hydrogen or cyano group; and $R_9$ is cyano group, carboxylic acid group, C1-C6 alkoxycarbonyl group, aryloxycarbonyl group, aryl group or substituted aryl group, which process comprises reacting a triindole derivative represented by the following general formula (8):

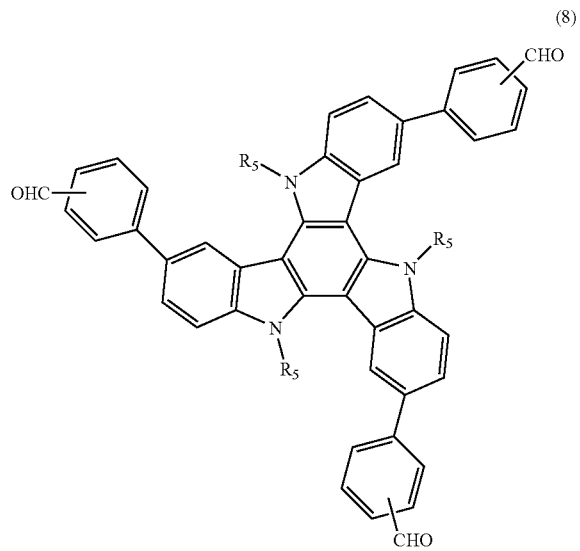
(8)

wherein $R_5$ has the same definition as given above, with a methylene compound represented by the general formula (9):

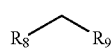
(9)

wherein $R_8$ and $R_9$ have the same definitions as give above.

6. A Sym-triindole vinyl derivative represented by the following general formula (11):

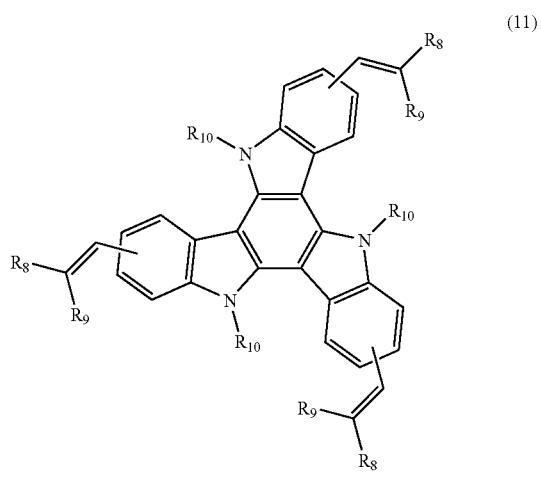
(11)

wherein $R_8$ is hydrogen or cyano group; $R_9$ is cyano group, carboxylic acid group, C1-C6 alkoxycarbonyl group, aryloxycarbonyl group, aryl group or substituted aryl group; and $R_{10}$ is C2-C12 alkyl group, substituted C2-C12 alkyl group, C2-C12 haloalkyl group or aryl C1-C6 alkyl group.

7. A process for producing a Sym-triindole derivative represented by the following general formula (11):

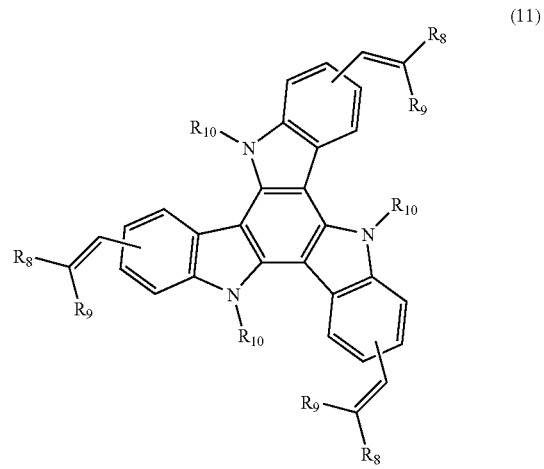
(11)

wherein $R_8$ is hydrogen or cyano group; $R_9$ is cyano group, carboxylic acid group, C1-C6 alkoxycarbonyl group, aryloxycarbonyl group, aryl group or substituted aryl group; and $R_{10}$ is C2-C12 alkyl group, substituted C2-C12 alkyl group, C2-C12 haloalkyl group or aryl C1-C6 alkyl group, which process comprises reacting an oxyindole compound represented by the following general formula (12):

(12)

wherein $R_{10}$ has the same definition as given above and X is halogen, with a phosphorus oxyhalide to obtain a Sym-halo-triindole derivative represented by the following general formula (13):

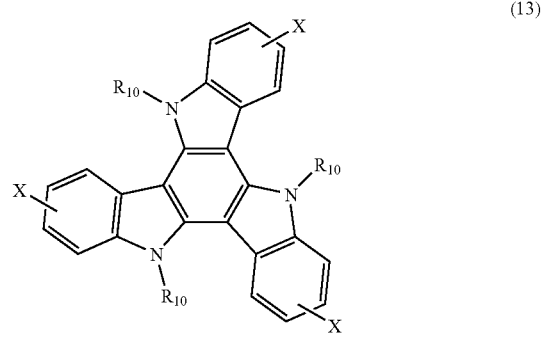
(13)

wherein $R_{10}$ and X have the same definitions as given above, subjecting the derivative of general formula (13) to formylation with a formylating agent in the presence of butyllithium to obtain a Sym-formyltriindole derivative represented by the following general formula (14):

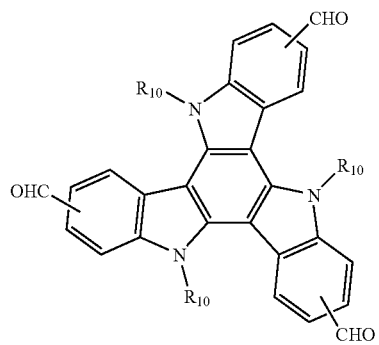
(14)

wherein $R_{10}$ has the same definition as given above, and reacting the derivative of general formula (14) with a methylene compound represented by the following general formula (9):

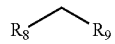
(9)

wherein $R_8$ and $R_9$ have the same definitions as given above.

8. A process for producing a Sym-triindole derivative represented by the following general formula (11):

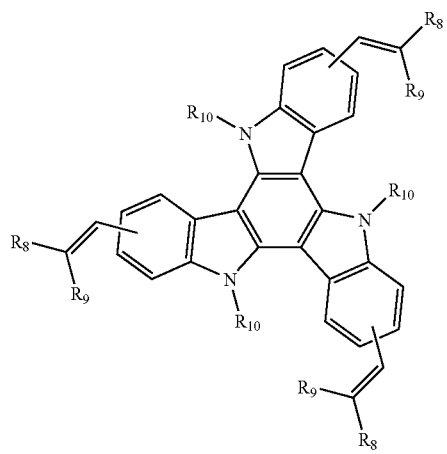
(11)

wherein $R_8$ is hydrogen or cyano group; $R_9$ is cyano group, carboxylic acid group, C1-C6 alkoxycarbonyl group, aryloxycarbonyl group, aryl group or substituted aryl group; and $R_{10}$ is C2-C12 alkyl group, substituted C2-C12 alkyl group, C2-C12 haloalkyl group or aryl C1-C6 alkyl group, which process comprises reacting a Sym-formyltriindole derivative represented by the following general formula (14):

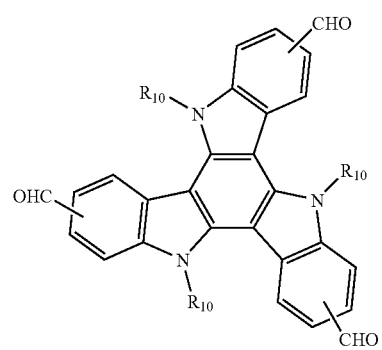
(14)

wherein $R_{10}$ has the same definition as given above, with a methylene compound represented by the following general formula (9):

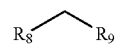
(9)

wherein $R_8$ and $R_9$ have the same definitions as given above.

9. A process for producing a Sym-formyltriindole derivative represented by the following general formula (14):

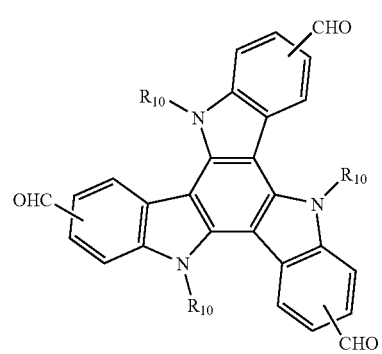
(14)

wherein $R_{10}$ is C2-C12 alkyl group, substituted C2-C12 alkyl group, C2-C12 haloalkyl group or aryl C1-C6 alkyl group), which process comprises subjecting a Sym-halo-triindole derivative represented by the following general formula (13):

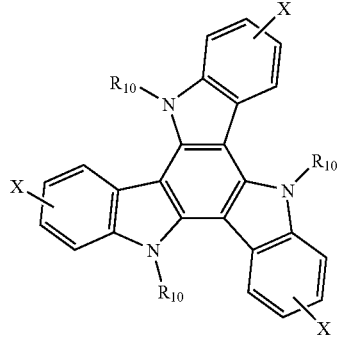
(13)

wherein $R_{10}$ has the same definition as given above and X is halogen, to formylation with a formylating agent in the presence of butyllithium.

10. A Sym-triindole derivative represented by the following general formula (15):

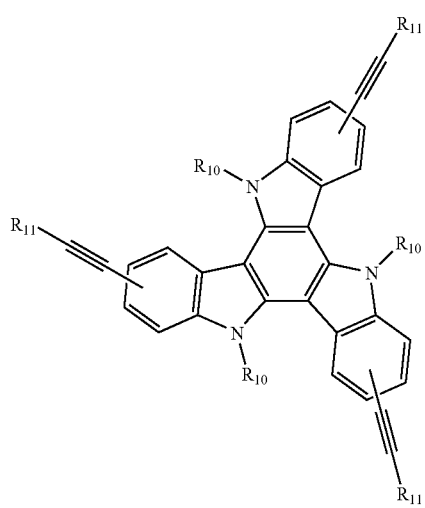
(15)

wherein $R_{10}$ is C2-C12 alkyl group, substituted C2-C12 alkyl group, C2-C12 haloalkyl group or aryl C1-C6 alkyl group; and $R_{11}$ is aryl group or substituted aryl group.

11. A process for producing a Sym-triindole derivative represented by the following general formula (15):

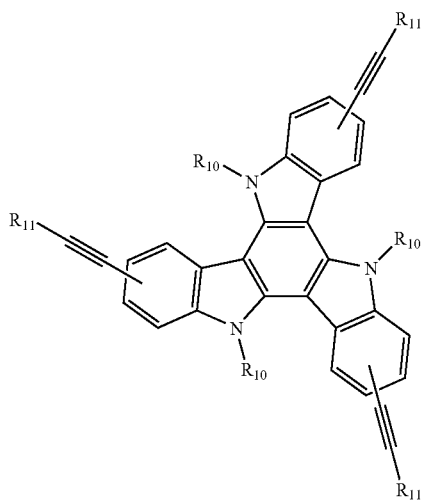
(15)

wherein $R_{10}$ is C2-C12 alkyl group, substituted C2-C12 alkyl group, C2-C12 haloalkyl group or aryl C1-C6 alkyl group; and $R_{11}$ is aryl group or substituted aryl group, which process comprises reacting a Sym-halo-triindole derivative represented by the following general formula (13):

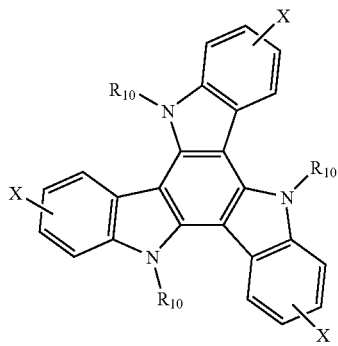
(13)

wherein $R_{10}$ has the same definition as given above and X is halogen with an acetylene derivative represented by the following general formula (16):

$$R_{11}R_{12} \quad (16)$$

wherein $R_{11}$ has the same definition as given above and $R_{12}$ is hydrogen or trimethylsilyl group.

* * * * *

UNITED STATES PATENT AND TRADEMARK OFFICE
CERTIFICATE OF CORRECTION

PATENT NO. : 7,632,954 B2  Page 1 of 1
APPLICATION NO. : 10/589534
DATED : December 15, 2009
INVENTOR(S) : Hidetaka Hiyoshi et al.

It is certified that error appears in the above-identified patent and that said Letters Patent is hereby corrected as shown below:

Column 40, line 32, "N-substituted5-halooxyindole" should read
-- N-substituted-5-halooxyindole --; and Column 48, lines 47-48, delete "$R_{11}R_{12}$" and insert the following formula:

-- $R_{11}\!=\!\!=\!\!R_{12}$   (16) --

Signed and Sealed this

Twenty-fifth Day of May, 2010

David J. Kappos
*Director of the United States Patent and Trademark Office*

UNITED STATES PATENT AND TRADEMARK OFFICE
CERTIFICATE OF CORRECTION

PATENT NO. : 7,632,954 B2  Page 1 of 1
APPLICATION NO. : 10/589534
DATED : December 15, 2009
INVENTOR(S) : Hiyoshi et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 464 days.

Signed and Sealed this

Twenty-first Day of December, 2010

David J. Kappos
*Director of the United States Patent and Trademark Office*